United States Patent [19]

Varma et al.

[11] Patent Number: 4,654,366
[45] Date of Patent: Mar. 31, 1987

[54] HYDROXAMIC ACIDS OF 7-OXABICYCLO[2.2.1]HEPTANE SUBSTITUTED ETHERS USEFUL AS ANTI-THROMBOTIC AGENTS

[75] Inventors: Ravi K. Varma, Belle Mead; Jagabandhu Das, Plainsboro, both of N.J.

[73] Assignee: E. R. Squibb & Sons, Inc., Princeton, N.J.

[21] Appl. No.: 829,639

[22] Filed: Feb. 14, 1986

[51] Int. Cl.[4] .................. A61K 31/34; A61K 31/557; C07D 307/00
[52] U.S. Cl. .................................... 514/469; 549/463
[58] Field of Search ......................... 549/463; 514/469

[56] References Cited

U.S. PATENT DOCUMENTS

| | | | |
|---|---|---|---|
| 4,143,054 | 3/1979 | Sprague | 260/346.22 |
| 4,187,236 | 2/1980 | Sprague | 260/346.22 |
| 4,220,594 | 9/1980 | Sprague | 260/345.9 |
| 4,228,180 | 10/1980 | Sprague | 424/285 |
| 4,254,044 | 3/1981 | Sprague | 260/347.8 |
| 4,537,981 | 8/1985 | Snitman et al. | 549/463 |

FOREIGN PATENT DOCUMENTS

| | | |
|---|---|---|
| 0043292 | 8/1982 | European Pat. Off. . |
| 0082646 | 6/1983 | European Pat. Off. . |
| 2039909 | 8/1980 | United Kingdom . |

*Primary Examiner*—Henry R. Jiles
*Assistant Examiner*—Bernard I. Dentz

*Attorney, Agent, or Firm*—Lawrence S. Levinson; Burton Rodney

[57] ABSTRACT

7-Oxabicycloheptane substituted ether or thio ether prostaglandin analogs are provided having the structural formula

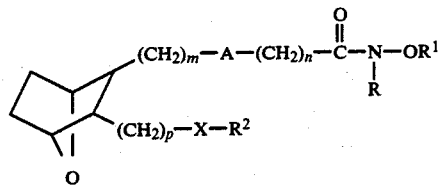

wherein A is O or

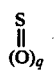

and X is O or

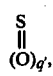

and including all stereoisomers thereof.

The compounds are inhibitors of $\Delta^5$-lipoxygenase and inhibitors of prostaglandin and leukotriene biosynthesis and as such are useful, for example, as antiallergy and antiinflammatory agents and also as antipsoriatic agents.

17 Claims, No Drawings

HYDROXAMIC ACIDS OF 7-OXABICYCLO[2.2.1]HEPTANE SUBSTITUTED ETHERS USEFUL AS ANTI-THROMBOTIC AGENTS

DESCRIPTION OF THE INVENTION

The present invention relates to hydroxamic acids of 7-oxabicyclo[2.2.1]heptane (hereinafter referred to as 7-oxabicycloheptane) substituted ether prostaglandin analogs which are inhibitors of $\Delta^5$-lipoxygenase and inhibitors of prostaglandin and leukotriene biosynthesis and as such as useful, for example, as antiallergy agents and antiinflammatory agents and also as antipsoriatic agents. These compounds have the structural formula

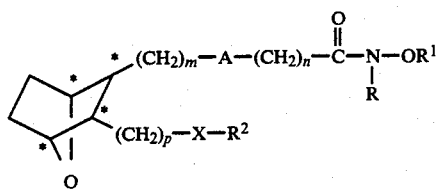

I and including all stereoisomers thereof, wherein
A is O or

q is 0, 1 or 2; m is 1 or 2; n is 1 to 8; p is 1 to 5; X is O or

q' is 0, 1 or 2; and wherein q' is 0, 1 or 2 where A is 0 (oxygen), and q' is 0 (zero) when A is S; R is H, lower alkyl, aryl, arylalkyl, cycloalkyl or cycloalkylalkyl; $R^1$ is H, lower alkyl, aryl, arylalkyl, cycloalkyl, alkanoyl or aroyl; and $R^2$ is lower alkyl, aryl, aralkyl, cycloalkyl, cycloalkylalkyl or lower alkenyl.

Thus, the compounds of the invention include the following types of compounds:

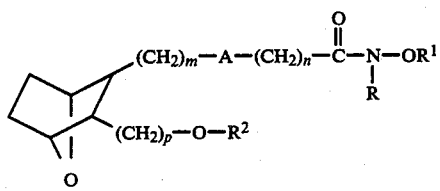

IA

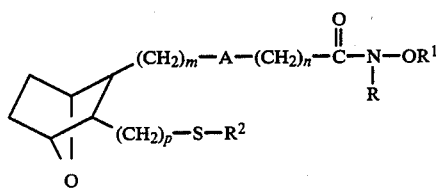

IB

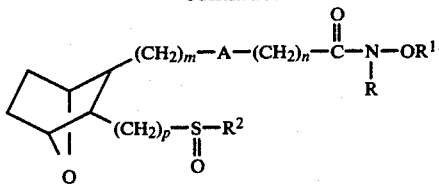

IC

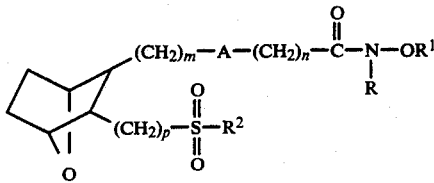

ID

The term "lower alkyl" or "alkyl" as employed herein includes both straight and branched chain radicals of up to 12 carbons, preferably 1 to 8 carbons, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various branched chain isomers thereof, and the like as well as such groups including a halo-substituent, such as F, Br, Cl or I or $CF_3$, an alkoxy substituent, an aryl substituent, an alkyl-aryl substituent, a haloaryl substituent, a cycloalkyl substituent or an alkylcycloalkyl substituent.

The term "cycloalkyl" includes saturated cyclic hydrocarbon groups containing 3 to 12 carbons, preferably 3 to 8 carbons, which include cyclopropyl, cyclobutyl, cyclopentyl, cyclohexyl, cycloheptyl, cyclooctyl, cyclodecyl and cyclododecyl, any of which groups may be substituted with 1 or 2 halogens, 1 or 2 lower alkyl groups and/or 1 or 2 lower alkoxy groups.

The term "aryl" or "Ar" as employed herein refers to monocyclic or bicyclic aromatic groups containing from 6 to 10 carbons in the ring portion, such as phenyl, naphthyl, substituted phenyl or substituted naphthyl wherein the substituent on either the phenyl or naphthyl may be 1 or 2 lower alkyl groups, halogens (Cl, Br or F), and/or lower alkoxy groups.

The term "aralkyl", "aryl-alkyl" or "aryl-lower alkyl" as used herein refers to lower alkyl groups as discussed above having an aryl substituent, such as benzyl.

The term "lower alkenyl" as used herein refers to straight or branched chain radicals of 2 to 12 carbons, preferably 2 to 6 carbons in the normal chain, which include one double bond in the normal chain, such as 2-propenyl, 3-butenyl, 2-butenyl, 4-pentenyl, 3-pentenyl, 2-hexenyl, 3-hexenyl, 2-heptenyl, 3-heptenyl, 4-heptenyl, 3-octenyl, 3-nonenyl, 4-decenyl, 3-undecenyl, 4-dodecenyl and the like.

The terms "alkanoyl" and "aroyl" refer to a lower alkyl group linked to a carbonyl group or an aryl group linked to a carbonyl group.

The term "halogen" or "halo" as used herein refers to chlorine, bromine, fluorine or iodine, with chlorine being preferred.

The terms "$(CH_2)_m$", "$(CH_2)_n$" and "$(CH_2)_p$" includes a straight or branched chain radical having 1 or 2 carbons in the normal chain in the case of $(CH_2)_m$, 1 to 8 carbons in the normal chain in the case of "$(CH_2)_n$" and 1 to 5 carbons in the normal chain in the case of "$(CH_2)_p$" and may contain one or more lower alkyl and/or halogen substituents. Examples of $(CH_2)_m$, $(CH_2)_n$ and $(CH_2)_p$ groups include

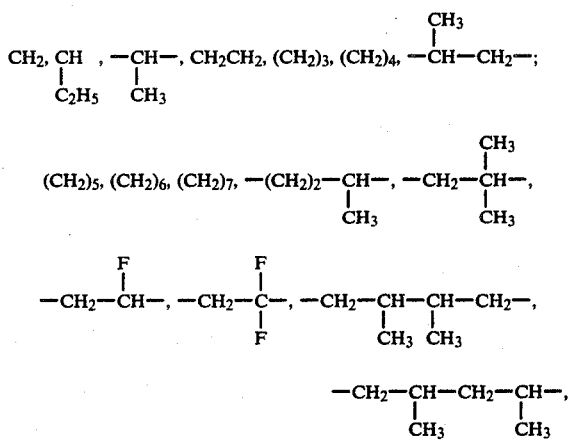

and the like.

Preferred are those compounds of formula I wherein m is 1 or 2, A is O or S, n is 3 to 5, p is 1, X is O or S, R is lower alkyl, R¹ is hydrogen, and R² is lower alkyl, such as hexyl, aryl, such as phenyl, or aralkyl such as benzyl.

The various compounds of the invention may be prepared as outlined below.

The 7-oxabicycloheptane ether compounds of formula I of the invention wherein X is O, m is 2, p is 1, A is O, and n is 1 to 8, that is, IE.

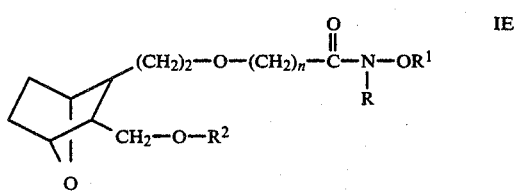

may be prepared starting with the cyanoalcohol II

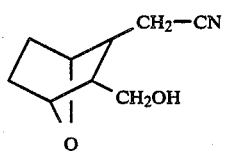

which is subjected to a benzylation reaction wherein compound II is reacted with a base such as NaH, NaOCH₃, KH, KOt—C₄H₉ and the like in the presence of an inert solvent, such as dimethylformamide, dimethoxyethane or tetrahydrofuran to form the mono benzylether compound III

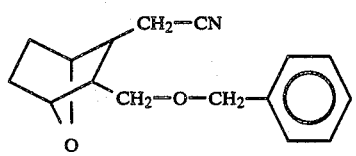

Compound III is reduced with diisobutyl aluminum hydride in the presence of an inert solvent, such as tetrahydrofuran, toluene or methylene chloride, to form the aldehyde IV

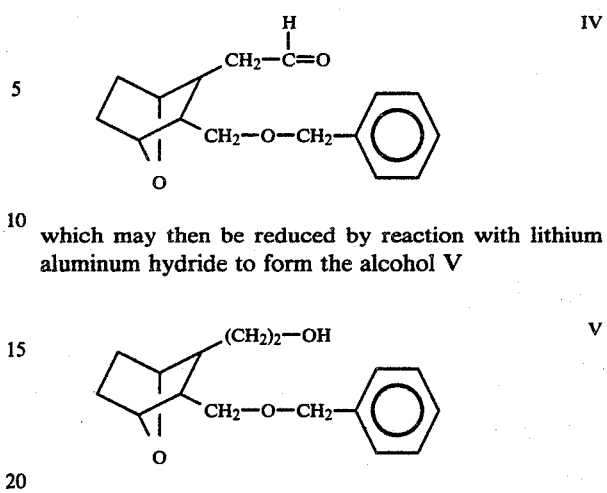

which may then be reduced by reaction with lithium aluminum hydride to form the alcohol V

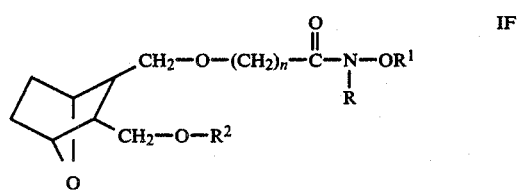

Compound V is then used to prepare the final products wherein m is 2 as will be described hereinafter.

The 7-oxabicycloheptane ether compounds of formula I of the invention wherein m is 1, n is 1 to 4, A is O, X is O, and p is 1, that is,

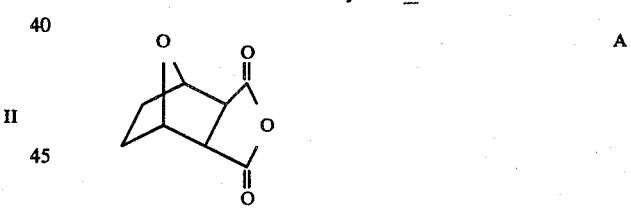

maybe prepared as follows.

Mesoanhydride A

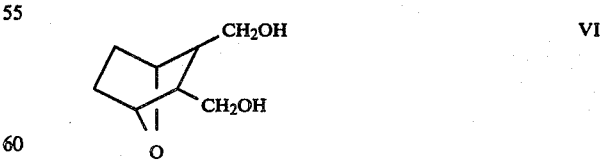

(prepared as described in U.S. Pat. Nos. 4,143,054 and 4,220,594) is reacted with a reducing agent such as lithium aluminum hydride or diisobutylaluminum hydride in the presence of an inert organic solvent such as tetrahydrofuran, toluene or ether to form diol VI which is subjected to a benzylation wherein compound VI is reacted with a base such as NaH, NaOCH₃, KH, KOt—C₄H₉ and the like and a benzyl halide such as benzylbromide in the presence of an inert solvent such as dimethylformamide, dimethoxyethane, tetrahydrofuran or benzene to form the monobenzylether VII

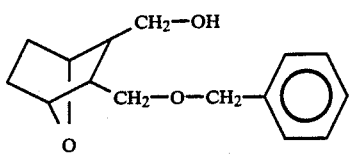

which is used to prepare compounds of formula I wherein $(CH_2)_m$ as described hereinafter.

Compound V or VII herein referred to as compounds V–VII, that is

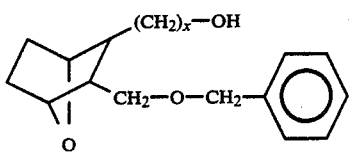

(wherein m is 2 where compound V is used and m is 1 where compound VII is used) is subjected to O-alkylation wherein it is reacted with a base such as KOH or NaOH and a silyl compound of the structure

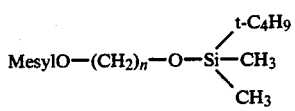

in the presence of an aromatic solvent such as xylene, toluene or mesitylene to form the silyl compound VIII

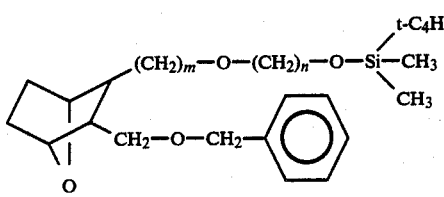

(m is 2 if V is used as the starting material or m is 1 if VII is used as the starting material) which is desilylated by reacting same with tetra-n-butyl ammonium fluoride in the presence of an inert solvent such as tetrahydrofuran, to form the alcohol IX

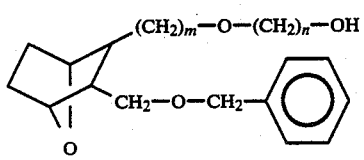

(wherein m is 2 or 1)

The alcohol IX is then made to undergo a Jones oxidation by reacting IX with chromium trioxide or other oxidizing agent such as pyridinium dichromate or pyridinium chlorochromate, in the presence of acetone or dimethylformamide to form the acid X,

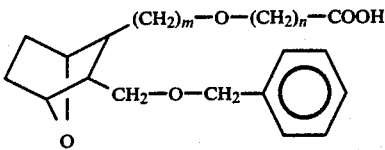

(where m is 2 or 1)

Acid X is then subjected to esterification by reacting acid X with diazomethane or other esterifying agent of the structure $RCHN_2$ (where R is an alkyl group) or an alkyl iodide and sodium bicarbonate in dimethylformamide to form the ester XI,

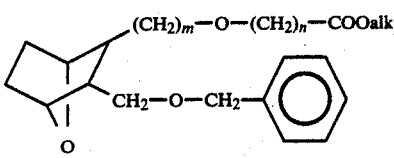

(wherein m is 2 or 1)

Ester XI is then subjected to hydrogenolysis by reacting ester XI with hydrogen in the presence of a catalyst such as palladium on carbon, platinum oxide and the like to form the alcohol XII

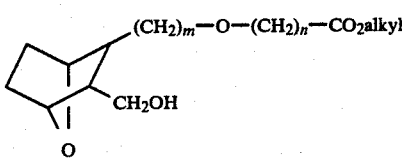

(wherein m is 2 or 1)

Other compounds of the invention within the scope of formula I may be prepared from alcohol XII as follows.

The alcohol XII is subjected to an ether formation reaction wherein XII is reacted with a strong base such as KOH, NaOH or LiOH in the presence of an inert organic solvent such as xylene, toluene, benzene or mesitylene, and then after partial removal of solvent, reacting with a sulfonate compound of the structure Mesyl—OR²      B or Tosyl—OR²      B' or a halide of the structure

R²X      B'' wherein X is Cl or Br, to form the ether XIII

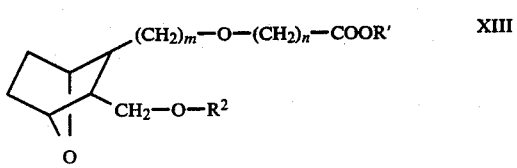

Ether XIII is then hydrolyzed by treating with strong aqueous base such as LiOH, KOH or NaOH to form the corresponding alkali metal salt and then acidifying with a strong acid such as HCl or oxalic acid to form XIV

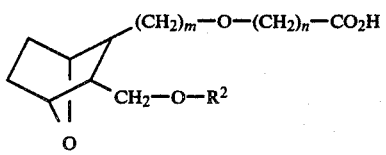 XIV

Acid XIV is then subjected to hydroxamate formation by treating a solution of XIV in an inert aromatic solvent such as benzene with oxalyl chloride and stirring the mixture at room temperature under nitrogen to form the acid chloride XV

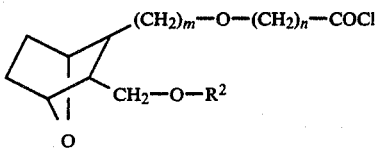 XV

The acid chloride XV is dissolved in an inert solvent such as tetrahydrofuran and added to a cold solution of XVA

 XVA in tetrahydrofuran and water in the presence of organic base such as triethylamine. The mixture is stirred under nitrogen atmosphere while being cooled in an ice bath, to form hydroxamate IE (where m is 2) or IE (where m is 1).

Compounds of formula I wherein A is S, m is 2, n is 1 to 8, X is O and p is 1, that is

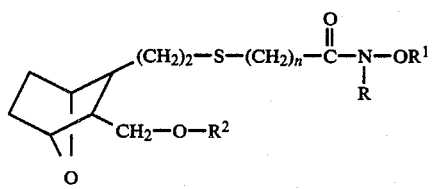 IG may be prepared starting with the diol VI

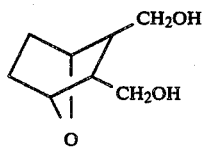 VI

Diol VI is etherified by reaction with a strong base such as sodium hydride in the presence of a solvent such as dimethylformamide and a sulfonate compound of the structure B or B' or a halide of the structure B" at temperatures of from about 50° to about 110° C., to form the ether XVII

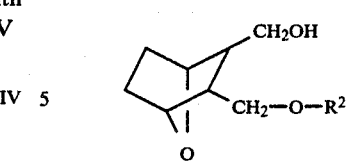 XVII

Ether XVII is next chlorinated by reacting with p-toluenesulfonyl chloride, lithium chloride and organic base such as pyridine to form XVIII

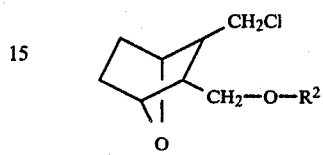 XVIII

Compound XVIII is then reacted with sodium cyanide, in the presence of a solvent such as dimethylsulfoxide or dimethylformamide at 90° to 95° C. for 2 to 24 hours, to form cyanide compound XIX

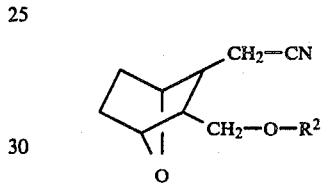 XIX

Cyanide compound XIX is then treated with diisobutylaluminum hydride (DiBAL) at reduced temperatures of from about −78° to about −20° C. under an inert atmosphere, such as argon, in inert solvents like toluene or tetrahydrofuran to form the aldehyde XX

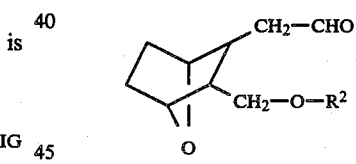 XX

Aldehyde XX is then treated with lithium aluminum hydride or other reducing agent such as sodium borohydride to form the hydroxyethyl compound XXI

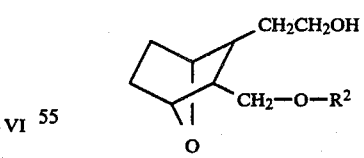 XXI

Hydroxyethyl compound XXI is used to make hydroxamate IG as follows.

Triphenylphosphine ((C₆H₅)₃P) is suspended in an inert solvent such as tetrahydrofuran, under a nitrogen atmosphere at a reduced temperature of from about 0° to about 20° C., and the suspension is treated with diisopropylazadicarboxylate. After 20 to 60 minutes, the suspension is treated with alcohol XXI and thiolacetic acid in a dry solvent such as tetrahydrofuran to form thioacetate XXII

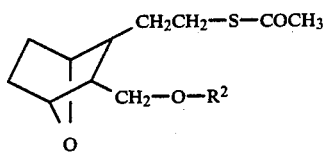

XXII

Thioacetate XXII is treated with lithium aluminum hydride under a nitrogen atmosphere at temperatures of from about 0° to about 20° C. to form the thiol XXIII

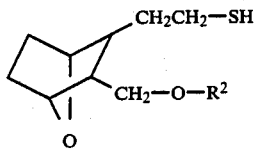

XXIII

Thiol XXXIII is then treated with halo compound XXIIIA

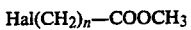

XXIIIA and base such as potassium carbonate in a dry inert solvent such as acetone under a nitrogen atmosphere to form ester XXIV

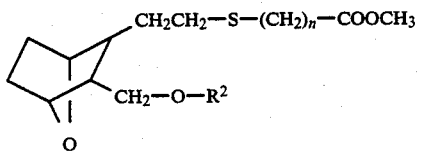

XXIV

The ester XXIV is then hydrolyzed to the corresponding acid by treatment with lithium hydroxide and the acid is converted to hydroxamate IG employing procedures as set out hereinbefore.

Compounds of formula I wherein A is S, m is 1, n is 1 to 8, X is O and p is 1, that is

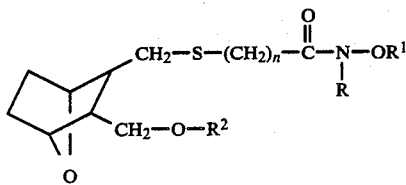

IH may be prepared by subjecting alcohol XXV

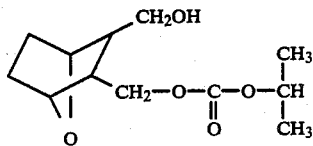

XXV (prepared as described in U.S. Pat. No. 4,515,972). to a modified Mitsunobu reaction wherein a mixture of the alcohol XXV and thiolacetic acid in an inert solvent such as tetrahydrofuran, ether or toluene is reacted with a mixture of triphenylphosphine and diisopropylazadicarboxylate in an inert organic solvent such as tetrahydrofuran, ether or toluene at temperatures of from about 0° C. to about 100° C. to form thioacetate XXVI.

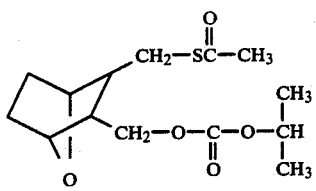

XXVI which is then reduced by treating with lithium aluminum hydride or diborane in the presence of an inert organic solvent such as tetrahydrofuran or other solvent such as ether to form the thiol XXVII

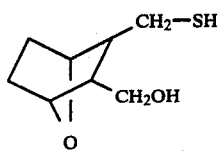

XXVII

Thiol XXVII is then alkylated by reacting with alkylating agent XXVIII

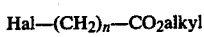

XXVII as described above with respect to thiol XXIV to form ester alcohol XXIX

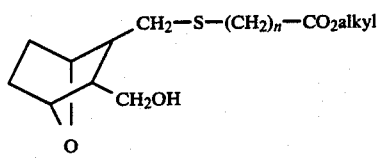

XXIX

Ester alcohol XXIX is then treated with reactant B, B' or B'', that is, in the presence of a strong base such as potassium hydroxide and an inert solvent such as xylene to form ether XXX

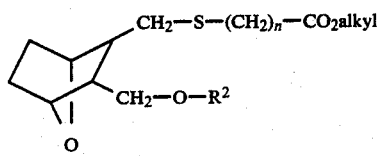

XXX which is then hydrolyzed by reaction with lithium hydroxide as described above to form acid XXXI

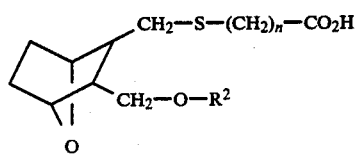

XXXI

Acid XXXI is then converted to the corresponding hydroxamate IH in a manner as described hereinbefore

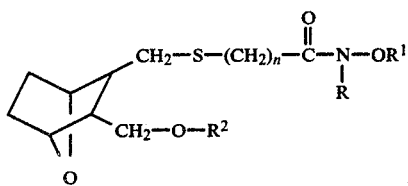

Compounds of formula I wherein X is O, A is S or O, m is 1 or 2, and p is 1 may be prepared by starting with the hydroxymethyl compound XII

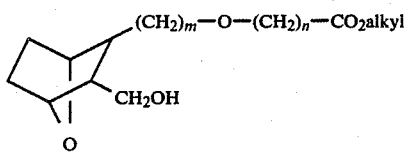

(wherein m is 2 or 1)
compound XXXII

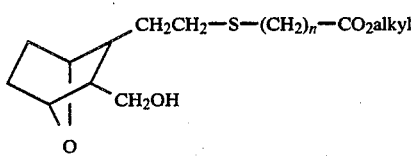

or

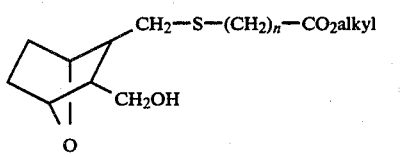

and subjecting one of the above hydroxymethyl compounds to a tosylation reaction, for example, by reacting the hydroxymethyl compound with tosyl chloride in pyridine and methylene chloride to form the corresponding tosylate XXXIII

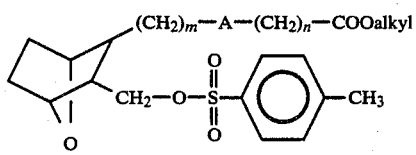

Thereafter, tosylate XXXIII is reacted with a thiol or mercaptan of the structure C

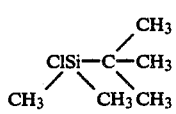

in the presence of potassium t-butoxide and a solvent such as tetrahydrofuran, dimethyl sulfoxide or dimethylformamide to form thioether ester compounds of the structure XXXIV. Alternatively, compounds of the type XII, XXXII or XXIX may be reacted with triphenylphosphine, a dialkylazadicarboxylate like diethylazadicarboxylate and a mercaptan of structure C to form thioether ester compounds of the structure XXXIV

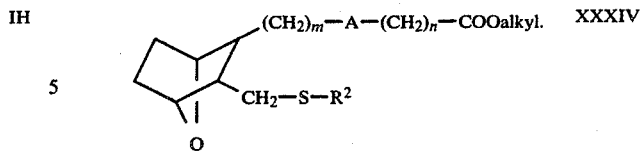

Ester compounds XXXIV may be hydrolyzed to the corresponding acids XXXV employing procedures as described herebefore

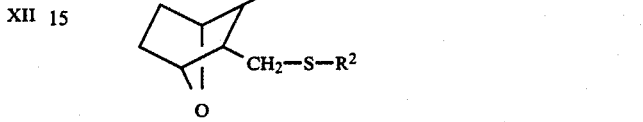

Intermediate compound XXXII, that is,

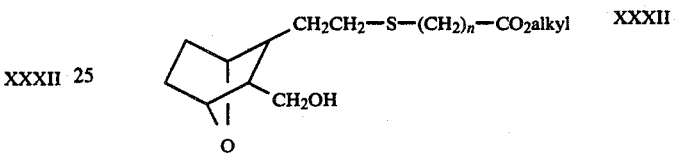

may be prepared as follows. Cyanoalcohol II is subjected to a silylation wherein compound II is reacted with a t-butyldimethylsilyl chloride having the structure D $$\begin{array}{c} CH_3 \\ ClSi-C-CH_3 \\ CH_3 \quad CH_3 CH_3 \end{array} \quad D$$

in the presence of dry dichloromethane and triethylamine and 4-dimethylaminopyridine to form the silyl ether XXXVI

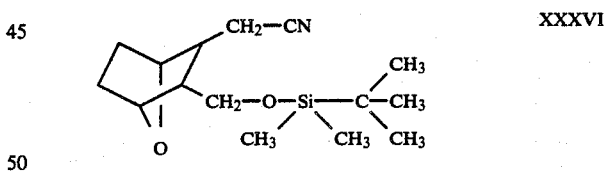

which is reduced by treating with a reducing agent such as diisobutylaluminum hydride, in the presence of an inert organic solvent such as toluene, tetrahydrofuran or methylene chloride in an inert atmosphere, at reduced temperatures of from about −78° C. to about 0° C. to form the aldehyde XXXVII

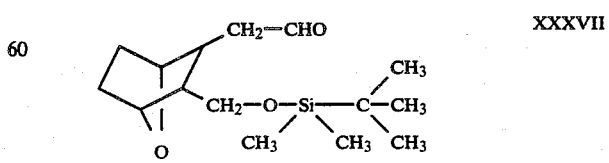

The aldehyde XXXVII is further reduced by treatment with a reducing agent such as lithiumaluminum hydride, sodium borohydride or lithium borohydride in the presence of an organic solvent such as tetrahydrofuran, ethanol or ether to form the alcohol XXXVIII

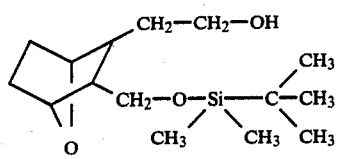
XXXVIII

The alcohol XXXVIII is then subjected to a modified Mitsunobu reaction wherein a mixture of the alcohol and thiolacetic acid in an inert solvent such as tetrahydrofuran, ether or toluene is reacted with a mixture of triphenylphosphine and diisopropylazo dicarboxylate in an inert organic solvent such as tetrahydrofuran, ether or toluene at temperatures of from about 0° C. to about 100° C. to form thioacetate XXXIX

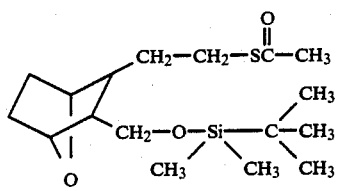
XXXIX

The silyl group is removed from thioacetate XXXIX by reacting VI with tetra-n-butylammonium fluoridde trihydrate in the presence of an inert organic solvent such as tetrahydrofuran or ether to form alcohol thioacetate XL

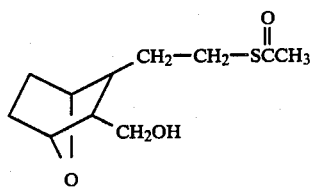
XL which is then deacetylated by treating with lithium aluminum hydride or bases like potassium carbonate or sodium methoxide in the presence of an inert organic solvent such as tetrahydrofuran or methanol to form thiol XLI

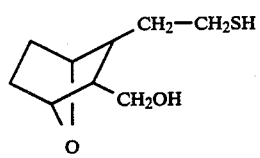
XLI

The thiol XLI is then alkylated by reacting same with an alkylating agent of the structure XXVIII

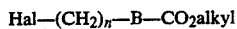

Hal—(CH$_2$)$_n$—B—CO$_2$alkyl      XXVIII in the presence of a base such as sodium or potassium hydride or potassium carbonate and an inert organic solvent such as acetone, THF or DMF, and reduced temperatures of from about 0° C. to about 50° C., to form alcohol XXXII

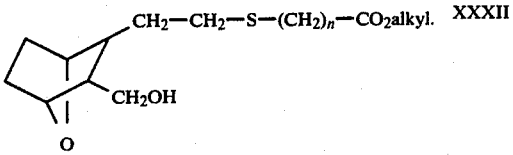
XXXII

Compounds of formula I wherein m is 1 and p is 2 to 5 may be prepared by subjecting aldehyde XLII

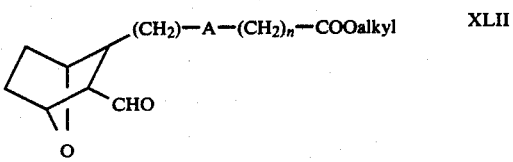
XLII wherein A is O or S
to a homologation sequence, such as Wittig reaction with (C$_6$H$_5$)$_3$P+Cl−CH$_2$OCH$_3$ followed by hydrolysis, (p−1) times, to form aldehyde XLIII

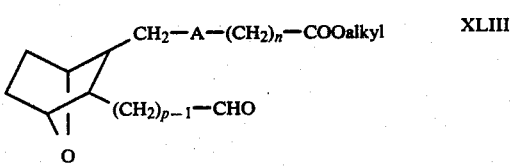
XLIII which is carried on to compounds of the invention where p is 2 to 5 by reducing aldehyde XLIII employing a reducing agent such as sodium borohydride in a solvent such as methanol to form alcohol ester XLIV

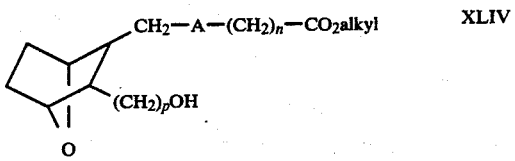
XLIV which is subjected to an etherification reaction with B, B' or B" as described above or to a thioetherification reaction with thiol C to form XLV

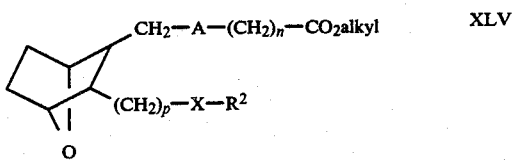
XLV which may be hydrolyzed to the corresponding acid XLVA employing procedures as set out hereinbefore.

Aldehyde XLII wherein A is O may be prepared from alcohol XII (wherein A is O) by carrying out a Collins oxidation wherein alcohol XII is reacted with a complex of CrO$_3$ with organic base such as pyridine, in dichloromethane or with pyridinium chlorochromate in a solvent such as methylene chloride.

Aldehyde XLII wherein A is S may be prepared from alcohol XXIX (wherein A is S) by subjecting such alcohol to a Corey-Kim oxidation wherein the appropriate alcohol in toluene is added to a mixture of dimethylsulfide and N-chlorosuccinimide in dry toluene or other inert organic solvent such as methylene chloride, and the mixture is stirred at 0° C. and then cooled to −25° C. After stirring at −25° C., triethylamine is added and the mixture is then warmed and purified to give aldehyde XLII.

Ether intermediate compounds wherein m is 2 and p is 2, 3, 4, or 5 may be prepared by oxidizing alcohol XII (wherein A is O) via a Collins oxidation technique as described hereinbefore or by oxidizing alcohol XXIX (wherein A is S) via a Corey-Kim oxidation or Swern oxidation as described hereinbefore to form aldehyde XLVI

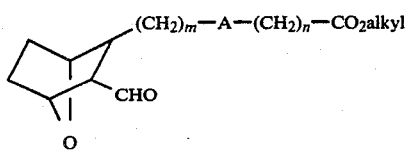

Aldehyde XLVI is then subjected to a homologation sequence such as a Wittig reaction with $(C_6H_5)_3P^+Cl^-CH_2OMe$ followed by hydrolysis, $(p-1)$ times, to form aldehyde XLVII

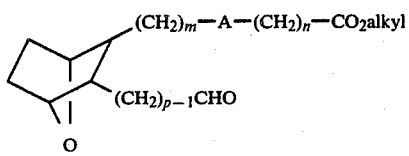

Aldehyde XLVII is then reduced to the corresponding alcohol XLVIII

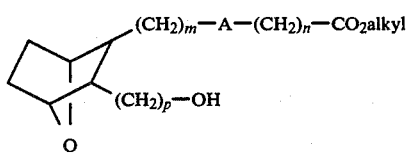

by reacting XLVIII with sodium borohydride in a solvent like methanol, ethanol or tetrahydrofuran. The alcohol XLVIII may then be subjected to an etherification reaction with B, B' or B" or to a thioetherification reaction with C to form the compounds of the invention.

Ether intermediate compounds of formula I wherein $R^2$ is aryl such as phenyl or substituted phenyl may also be prepared by reacting the alcohol XII, XXXII, XXIX, XLII or XLIV with triphenylphosphine and diethylazodicarboxylate in solution with an inert solvent such as THF, and thereafter without isolating any products, reacting the above reaction mixture with an aryl alcohol wherein the hydroxy group is directly attached to the aromatic ring, such as phenol or a substituted phenol, under an inert atmosphere, such as argon or nitrogen, to form the ester of the structure XLIX

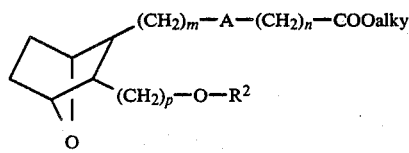

(wherein $R^2$ is phenyl or substituted phenyl).

The above esters can be converted to the free acid, that is, to L

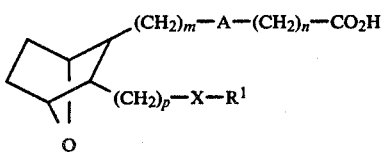

by treating the esters with an alkali metal hydroxide, such as lithium or sodium hydroxide to form the corresponding alkali metal salt (wherein R is an alkali metal such as Na, Li or K) followed by acidification with an acid, such as dilute hydrochloric acid or oxalic acid to form the acid L.

The acids XXXV, XLVA and L may then be converted to the corresponding hydroxamates employing procedures disclosed hereinbefore.

To form compounds of formula I wherein X is

the sulfide derivative of formula I wherein X is S and A is O is subjected to an oxidation reaction, for example, by reacting same with aqueous sodium periodate, in the presence of water, methanol or tetrahydrofuran, to form the corresponding sulfinyl derivative

and sulfonyl derivative

Where A is S and X is S, oxidation of S in the lower side chain will cause similar oxidation of S in the upper side chain. The sulfinyl and sulfonyl derivatives may be separated by chromatography or other conventional separation procedures.

The compounds of this invention have four centers of asymmetry as indicated by the asterisks in formula I. However, it will be apparent that each of the formulae set out above which do not include asterisks still represent all of the possible stereoisomers thereof. All of the various stereoisomeric forms are within the scope of the invention.

The various stereoisomeric forms of the compounds of the invention, namely, cis-exo, cis-endo and all trans forms and stereoisomeric pairs may be prepared as shown in the working Examples which follow and by employing starting materials and following the procedures as outlined in U.S. Pat. No. 4,143,054. Examples of such stereoisomers are set out below.

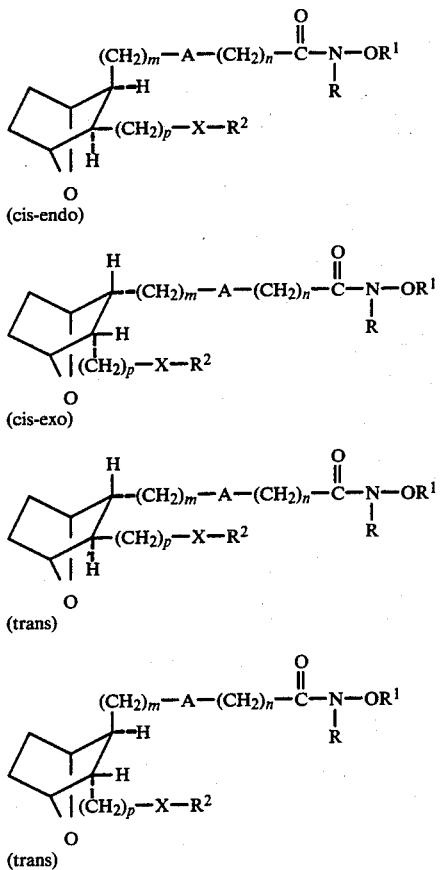

The nucleus in each of the compounds of the invention is depicted as

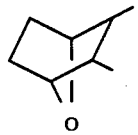

for matter of convenience; it will also be appreciated that the nucleus in the compounds of the invention may be depicted as

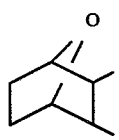

It will also be understood that the position of the bonds in the above nuclei are not intended to identify particular isomers but are intended to generally depict all isomers.

The compounds of this invention are cardiovascular agents useful as platelet aggregation inhibitors, such as inhibiting arachidonic acid-induced platelet aggregation (e.g., for treatment of thrombotic disease, such as coronary or cerebral thromboses) and in inhibiting broncho-constriction as induced by asthma. They are also selective thromboxane $A_2$ receptor antagonists and synthetase inhibitors, e.g., having a vasodilatory effect for treatment of myocardial ischemic disease, such as angina pectoris. In addition, the compounds of the invention are thromboxane synthetase inhibitors and they may also be used for preventing gastrointestinal ulcer formation. They also increase the amount of endogenous prostacyclin and therefore may be used for controlling tumor cell metastasis or as antihypertensive agents.

The compounds of the invention are also arachidonic acid cyclooxygenase inhibitors. In addition, the compounds of the invention are useful as analgesic agents in the manner of aspirin and indomethacin as indicated by reaction thresholds to pressure in edematous hindpaws [Ref: Winter et al, J. Pharmacol, Exp. Ther. 150: 165 1965] and as antiinflammatory agents in mammals, as indicated by carrageenin-induced edema in the rat [Ref: Winter et al., J. Pharmacol., Exp. Ther. 141: 369, 1963]. They may be used to decrease joint swelling, tenderness, pain and stiffness in conditions such as rheumatoid arthritis.

The compounds of this invention may also be used in combination with a cyclic AMP phosphodiesterase (PDE) inhibitor such as theophylline or papaverine in the preparation and storage of platelet concentrates.

In addition, the compounds of the invention are $\Delta^5$-lipoxygenase inhibitors and prevent prostaglandin and leukotriene $C_4$ formation in macrophages (Samuelsson, B., Science, Vol. 220, p. 568–575, 1983). The administration of compounds of this invention to humans or animals provides a method for treating allergy of a reagin or non-reagin nature. Asthma is preferably treated but any allergy wherein leukotrienes are thought to be involved as pharmacological mediators of anaphylaxis can be treated. For example, the compounds of this invention can be used for treatment of such conditions as allergic rhinitis, food allergy and urticaria as well as asthma. In addition, the compounds of the invention are useful as antipsoriatic agents.

The compounds of the invention can be administered orally or parenterally to various mammalian species known to be subject to such maladies, e.g., humans, cats, dogs, and the like in an effective amount within the dosage range of about 1 to 100 mg/kg, preferably about 1 to 50 mg/kg and especially about 2 to 25 mg/kg on a regimen in single or 2 to 4 divided daily doses.

The compounds of the invention may also be administered topically to any of the above mammalian species in amounts of from about 0.1 to 10 mg/kg in single or 2 to 4 divided daily doses.

The active substance can be utilized in a composition such as tablet, capsule, solution or suspension containing about 5 to about 500 mg per unit of dosage of a compound or mixture of compounds of formula I. They may be compounded in conventional matter with a physiologically acceptable vehicle or carrier, excipient, binder, preservative, stabilizer, flavor, etc. as called for by accepted pharmaceutical practice. Also as indicated in the discussion above, certain members additionally serve as intermediates for other members of the group.

The following Examples represent preferred embodiments of the invention. Unless otherwise indicated, all temperatures are expressed in °C.

EXAMPLE 1

[1R-(1α,2β,3β,4α)]-4-[[[3-[(Hexyloxy)methyl]-7-oxabicyclo[2.2.1]hept-2-yl]ethyl]thio]-N-hydroxy-N-methylbutanamide

A.
(1α,2β,3β,4α)-cis-exo-7-oxabicyclo[2.2.1]heptane-2,3-dimethanol

To a suspension of 11.4 g lithium aluminum hydride (300 mmole, 1.6 eq) in 400 ml of dry THF at 0° C. was added dropwise a solution of 32 g cis-exo 7-oxabicyclo[2.2.1]heptane-2,3-dicarboxylic anhydride (cis-exo-mesoanhydride) (190 mmole) in 400 ml of dry tetrahydrofuran (THF) over a period of 1 hour. The reaction mixture was stirred at 25° C. for 18 hours, cooled to 0° C. and quenched by slow addition of a saturated Na$_2$SO$_4$ solution and filtered. The solid was washed with three 100 ml portions of CH$_2$Cl$_2$. The combined organic layer was dried over MgSO$_4$ and concentrated to give 32 g of title diol as a colorless solid.

B.
(1α,2β,3β,4α)-2-[[(Chlorocarbonyl)oxy]methyl]-3-(hydroxy)methyl-7-oxabicyclo[2.2.1]heptane To a solution of 10 g Part A diol (63.2 mmole) in 40 ml dry THF at 0° C. was added with stirring 55 ml of a 12.5% by weight solution of phosgene in toluene (63.2 mmole, 1 eq.) dropwise over a period of 30 minutes. Argon was then bubbled through the reaction mixture for 15 minutes. The mixture was concentrated to give title compound as a crude oil.

C.
(1α,2β,3β,4α)-2,3-Bis(hydroxymethyl)-7-oxabicyclo[2.2.1]heptane, 2,3-cyclic carbonate Part B oil was dissolved in 30 ml of dry CH$_2$Cl$_2$ and cooled to −50° C. To this solution was added dropwise a solution of 10 ml pyridine in 10 ml CH$_2$Cl$_2$. It was stirred for 10 minutes and quenched with H$_2$O. The mixture was extracted thoroughly with CH$_2$Cl$_2$. The organic extract was dried over MgSO$_4$ and concentrated to give the title cyclic carbonate as a crystalline solid (10.7 g).

D.
(1α,2β,3β,4α)-2-Hydroxymethyl-3-[[[(1-methylethyl)oxy]carbonyl]oxy]methyl-7-oxabicyclo[2.2.1]heptane A mixture of 10.7 g Part C cyclic carbonate (58.1 mmole) in 100 ml isopropanol was refluxed for 24 hours. Excess isopropanol was removed under reduced pressure to give 14.4 g title hydroxycarbonate as a viscous oil.

E.
(1α,2β,3β,4α)-2-Hydroxymethyl-3-[[[(1-methylethyl)oxy]carbonyl]oxy]methyl-7-oxabicyclo[2.2.1]heptane, 2-[4-methyl(phenyl)]sulfonic acid ester To a solution of 19.7 g Part D hydroxycarbonate (80 mmole) in 30 ml CH$_2$Cl$_2$ and 12.8 ml pyridine (160 mmole, 2 eq.) was added 18.5 g of p-toluenesulfonyl chloride (96 mmole, 1.2 eq.). The mixture was stirred at 25° C. for 36 hours, then diluted with 200 ml ether, and washed with 100 ml brine. The organic layer was dried over MgSO$_4$ and concentrated to give 32.8 g of crude title tosylate as an oil.

F.
(1α,2β,3β,4α)-2-Cyanomethyl-3-[[[(1-methylethyl)oxy]carbonyl]oxy]methyl-7-oxabicyclo[2.2.1]heptane To a solution of 24.0 g crude Part E tosylate (60 mmole) in 20 ml DMSO was added with stirring 6.0 g powdered sodium cyanide (120 mmole, 2 eq.). The mixture was heated at 90°–95° C. for 1.5 hours under an argon atmosphere. The cooled mixture was diluted with 50 ml water and extracted with five 100 ml portions of ether. The ethereal extracts were dried over anhydrous MgSO$_4$ and filtered through a bed of florosil. The filtrate was concentrated, and the residue was recrystallized with ether/hexanes to give 8.4 g title cyanocarbonate as a light yellow crystalline solid.

G.
[1R-(1α,2β,3β,4α)]-2-Cyanomethyl-3-hydroxymethyl-7-oxabicyclo[2.2.1]heptane To 8.4 g Part F cyanocarbonate (33.2 mmole) was added 75 ml of a 1% solution of potassium carbonate in methanol-water (2:1). The reaction mixture was stirred at 25° C. for 6 hours then acidified with 2N HCl solution, saturated with sodium chloride and extracted with six 100 ml portions of CH$_2$Cl$_2$. The combined organic layer was dried over anhydrous MgSO$_4$ and concentrated to give 5.5 g of crude title cyanoalcohol (compound II) as a light yellow oil.

H.
[1R-(1α,2β,3β,4α)]-2-Cyanomethyl-3-[[[(1,1-dimethyl)ethyl]dimethyl]silyl]oxy-7-oxabicyclo[2.2.1]heptane To a solution of 5.0 g Part G alcohol (30 mmole) in 50 ml of dry CH$_2$Cl$_2$ and 10 ml of triethylamine (70 mmole, 3.3 eq.) at 0° C. was added with stirring 490 mg 4-dimethylaminopyridine (4 mmole) and 5.28 g t-butyldimethylsilylchloride (35 mmole, 1.16 eq.). The reaction mixture was slowly warmed to 25° C. and stirred for 18 hours, then diluted with 200 ml ether, and filtered through a small bed of anhydrous MgSO$_4$. The filtrate was concentrated. Purification was done on a silica gel column, eluting with 15% ethyl acetate in hexanes to give 10.25 g of title silyl ether as a light yellow oil.

I.
[1R-(1α,2β,3β,4α)]-2-[[[3-[(1,1-dimethyl)ethyl]dimethyl]silyl]oxy-7-oxabicyclo[2.2.1]hept-2-yl]acetaldehyde To a solution of 10.0 g of Part H (26.2 mmole) in 30 ml of dry toluene at −78° C. under an argon atmosphere was added dropwise 25 ml of a 25% by weight solution of diisobutylaluminumhydride (44 mmole) in toluene. The mixture was stirred at −78° C. for 4 hours, quenched at −78° with a saturated solution of ammonium chloride, warmed to 0° C. and acidified with 1N HCl solution, extracted with three 100 ml portions of CH$_2$Cl$_2$, dried over anhydrous MgSO$_4$ and concentrated to give 9.3 g of crude title aldehyde.

J.
[1R-(1α,2β,3β,4α)]-2-[[[3-(3-(1,1-dimethyl)ethyl]dimethyl]silyl]oxy-7-oxabicyclo[2.2.1]hept-2-yl]ethanol To 9.3 g crude Part I aldehyde (32.7 mmole) in 30 ml of dry THF at 0° C. under an argon atmosphere was added portionwise 1.0 g lithium aluminum hydride (26.0 mmole, 3.2 eq.) with stirring. The reaction mixture was stirred while being warmed to 25° C. over a period of 1 hour, quenched by slow addition of a saturated sodium sulfate solution at 0° C., dried over anhydrous MgSO4 and filtered. The solid was washed with CH2Cl2. The combined filtrate was concentrated to give a crude oil. This oil was purified on a silica gel column, eluting with 30% EtOAc in hexanes to give 8.55 g title alcohol as a colorless oil.

K.
[1R-(1α,2β,3β,4α)]-2-[(Acetylthio)ethyl]-3-[[[(1,1-dimethyl)silyl]oxy-7-oxabicyclo[2.2.1]heptane To a solution of 5.25 g triphenylphosphine (20 mmole, 2 eq.) in 60 ml dry THF at 0° C. was added dropwise 4.16 g diisopropylazodicarboxylate (20 mmole, 2 eq.) over a period of 15 minutes. The mixture was stirred at 0° C. for 30 minutes and a solution of 2.6 g Part J alcohol (10 mmole) and 1.45 ml of thiolacetic acid (20 mmole, 2 eq.) in 10 ml dry THF was add dropwise. The reaction mixture was stirred at 0° C. for 1 hour and at 25° C. for 3 hours and then concentrated. The residue was triturated with ether/hexane, filtered, and the filtrate was concentrated and purified on a silica gel column, eluting with 10% EtOAc in hexanes to give 2.3 g title thioacetate as a light yellow oil.

L.
[1R-(1α,2β,3β,4α)]-2-[[3-(Acetylthio)ethyl]-7-oxabicyclo[2.2.1]hept-2-yl]methanol To a solution of 2.3 g Part K thioacetate (6.7 mmole) in 20 ml dry THF at 0° C. was added 2.23 g tetra-n-butylammoniumfluoride trihydrate (7.07 mmole, 1.05 eq.) in 5 ml dry THF. The reaction mixture was warmed to 25° C., stirred for 18 hours, diluted with 100 ml ether, washed with 30 ml saturated NaHCO3 solution, dried over anhydrous MgSO4 and concentrated to give a crude oil. Purification was done on a silica gel column, eluting with 20% EtOAc in hexane and 50% EtOAc in hexane to give 1.22 g of title alcohol thioacetate as a colorless oil.

M.
[1R-(1α,2β,3β,4α)]-2-[[3-(Mercaptoethyl)-7-oxabicyclo[2.2.1]hept-2-yl]methanol To a slurry of 200 mg of lithium aluminumhydride (5.27 mmole, 4 eq.) in 20 ml dry THF at 0° C. was added dropwise a solution of 1.22 g of Part L thioacetate (5.3 mmole) in 5 ml THF under an argon atmosphere. The reaction mixture was stirred at 0° C. for 1 hour and quenched with a saturated sodium sulfate solution, dried with anhydrous MgSO4 and filtered. The filtrate was concentrated to give 900 mg title thiol as a colorless oil.

N.
[1R-[1α,2β,3β(1E,3R),4α]]-4-[[2-(3-Hydroxymethyl)-7-oxabicyclo[2.2.1]hept-2-yl]ethyl]thio]-2-butenoic acid, methyl ester To a slurry of 1.38 g of dried and powdered potassium carbonate (10 mmole, 2.1 eq.) in 20 ml dry acetone at 0° C. was added a solution of 900 mg Part M thiol (4.8 mmole) in 5 ml acetone, followed by 1.75 ml of methyl-4-bromocrotonate (15 mmole, 3 eq.). The reaction mixture was stirred at 0° C. for 10 hours then diluted with 100 ml ether and filtered through a pad of anhydrous MgSO4. The filtrate was concentrated. The residue was purified on a silica gel column, eluting with 20% EtOAc in hexane and 50% EtOAc in hexane to give 823 mg of title ester as a colorless oil.

O.
[1R-(1α,2β,3β,4α)]-4-[[2-(3-Hydroxymethyl)-7-oxabicyclo[2.2.1]hept-2-yl]ethyl]thio]butanoic acid, methyl ester A mixture of 570 mg of Part N olefin ester (2.0 mmole), and 600 mg of 10% palladium over carbon in 10 ml methanol was shaken in a Parr bottle under 40 psi hydrogen pressure, at 25° C. for 18 hours and was filtered. The filtrate was concentrated to give 470 mg of the title ester as an oil.

P.
[1R-(1α,2β,3β,4α)]-4-[[[3-[(Hexyloxy)methyl]-7-oxabicyclo[2.2.1]hept-2-yl]ethyl]thio]butanoic acid, hexyl ester A suspension of 583 mg of powdered potassium hydroxide (9.7 mmole, 10 eq.) in 100 ml of dry xylene was heated to reflux and 50 ml of xylene was distilled off. To the solution was slowly added 1.7 g of hexyl mesylate (9.7 mmole, 10 eq.) and Part O alcohol (0.97 mmol) in xylene (20 ml). The mixture was refluxed for 2 hours, cooled to 25° C., diluted with 200 ml of ether and washed with two 50 ml portions of H2O. The organic layer was dried over anhydrous MgSO4 and concentrated. The residue was purified on a silica gel column, eluting with 20% EtOAc in hexane to give the title compound as an oil (contaminated with small amount of hexyl mesylate).

Q.
[1R-(1α,2β,3β,4α)]-4-[[[3-[(Hexyloxy)methyl]-7-oxabicyclo[2.2.1]hept-2-yl]ethyl]thio]butanoic acid To 200 mg of crude Part P ester (ca. 0.45 mmole) in 80 ml of THF and 20 ml of H2O saturated with argon at 0° C. was added 4.5 ml of a 1M lithium hydroxide solution. The mixture was stirred at 25° C. for 20 hours and concentrated. The residue was diluted with 10 ml of H2O and acidified to pH 3 with a saturated aqueous solution of oxalic acid. The aqueous solution was extracted with three 40 ml portions of ether. The combined organic layer was washed with two 40 ml portions of H2O, dried over anhydrous MgSO4 and concentrated. The residue was purified on a silica gel column, eluting with a gradient of pentane/ether to yield 148 mg of title acid.

TLC: Silica gel; MeOH/CH2Cl2 (7:93); $R_f$~0.55.
Anal Calcd for $C_{19}H_{34}O_4S$: C, 63.64; H, 9.56; S, 8.94. Found: C, 63.41; H, 9.52; S, 8.70.

R.
[1R-(1α,2β,3β,4α)]-4-[[[[3-(Hexyloxy)methyl]-7-oxabicyclo[2.2.1]hept-2-yl]methyl]thio]-N-hydroxy-N-methyl butanamide A solution of Part Q acid (1.82 mmole) and oxalyl chloride (3.6 mmole) in dry benzene (10 ml) is cooled down to 0° (ice-water bath), treated with a solution of dimethylformamide (3 drops) in benzene and stirred at 0° for 30 minutes under nitrogen and at room temperature for one hour. The excess oxalyl chloride and solvent are blown off under a stream of nitrogen while heating the flask in a warm water bath and the residual oil is dried in vacuo (pump) for one hour. This acid chloride is dissolved in dry tetrahydrofuran (3.5 ml) and added dropwise under stirring into a cold solution (~0°, ice-water) of 98% methylhydroxylamine hydrochloride (318.7 mg, 3.74 mmole) and triethylamine (0.92 ml, 7.48 mmole) in tetrahydrofuran (4.6 ml) and water (4.6 ml). The mixture is stirred at 0° for 30 minutes, diluted with water (25 ml) and extracted twice with dichloromethane (125 ml). The combined organic extracts are washed with 1N HCl (25 ml), 5% NaHCO$_3$ (12 ml) and brine (20 ml), dried (anhydrous MgSO$_4$), filtered and evaporated to dryness giving an oil containing the desired product.

EXAMPLE 1A (1α,2β,3β,4α)-5-[[[3-[(Hexyloxymethyl]-7-oxabicyclo[2.2.1]hept-2-yl]methyl]thio]-N-hydroxy-N-methylpentanamide

A.

(1α,2β,3β,4α)-cis-exo-[[3-Isopropyloxycarbonyloxymethyl-7-oxabicyclo[2.2.1]hept-2-yl]methyl]thioacetate To a solution of 10.5 g of triphenylphosphine (40 mmole) in 100 ml of dry THF at 0° C. was added dropwise 95% pure diisopropylazo-dicarboxylate (40 mmole) over a period of 15 minutes. After stirring for 30 minutes, a solution of 4.88 g of Example 1 title D alcohol carbonate (20 mmole) and 1.43 ml of distilled thiol acetic acid (20 mmole) in 10 ml of dry THF was added dropwise over a period of 20 minutes. The minutes was stirred at 0° C. for 30 minutes and at 25° C. for 1 hour, and then concentrated. The residue was triturated with ether/hexane, and then filtered. The filtrate was concentrated and purified on a silica gel column, eluting with 5% ethyl acetate in hexane followed by 10% ethyl acetate in hexane to give 5.12 g of title thioacetate as a colorless crystalline solid.

B.

(1α,2β,3β,4α)-cis-exo-[3-(Hydroxymethyl)-7-oxabicyclo[2.2.1]hept-2-yl]-2-methanethiol To a slurry of 400 mg of 95% pure lithium aluminum hydride (13 mmole) in 25 ml of dry THF at 0° C. under an argon atmosphere was added dropwise a solution of 1.9 g of title A thioacetate (6 mmole) in 100 ml of dry THF. The mixture was stirred at 0° C. for 30 minutes and at 25° C. for 1 hour and then quenched with a saturated sodium sulfate solution. The mixture was dried with anhydrous MgSO$_4$ and filtered. The filtrate was concentrated to give the crude title thio-alcohol as an oil.

This oil was used in the next step without purification.

C.

(1α,2β,3β,4α)-5-[[[3-(Hydroxymethyl)-7-oxabicyclo[2.2.1]hept-2-yl]methyl]thio]pentanoic acid, methyl and ethyl esters To a slurry of 480 mg of 50% sodium hydride in mineral oil (10 mmole) in 20 ml of dry THF at 0° C. was added dropwise a solution of 820 mg of title B thioalcohol (4.71 mmole) in 5 ml of dry THF under nitrogen. After stirring for 20 minutes at 0° C., a solution of 3.17 ml of ethyl-5-bromo-valerate (20 mmole) was added dropwise. The reaction mixture was stirred at 0° C. for 2 hours and then quenched with a saturated solution of ammonium chloride. The layers were separated. The aqueous layer was acidified with a 2N HCl solution and extracted several times with CH$_2$Cl$_2$. The combined organic layer was dried over anhydrous MgSO$_4$ and concentrated. The residue was diluted with 25 ml of ether and treated with an etheral solution of diazomethane.

Purification was done on a silica gel column, eluting with 10% EtOAc/hexane followed by 20% EtOAc/hexane to give 540 mg of a mixture of title methyl and ethyl esters as a colorless oil.

D.

(1α,2β,3β,4α)-5-[[[3-[(Hexyloxy)methyl]-7-oxabicyclo[2.2.1]hept-2-yl]methyl]thio]pentanoic acid, hexyl ester To a solution of 583 mg of powdered potassium hydroxide (9.7 mmole) in 50 ml of dry xylene was added a solution of 266.5 mg of title C alcohol (0.97 mmole) in 50 ml of dry xylene. The mixture was heated to reflux and 50 ml of xylene was distilled off. To the cooled remaining solution was added 1.7 g of hexyl mesylate (9.7 mmole, 10 eq.). The reaction was carried out under an atmosphere of nitrogen. The mixture was refluxed for 2 hours then cooled to 25° C., diluted with 200 ml of ether and washed with two 50 ml portions of H$_2$O. The organic layer was dried over anhydrous MgSO$_4$ and concentrated. The residue was purified on a silica gel column, eluting with 20% EtOAc in hexanes to give 200 mg of title oil (contaminated with a small amount of hexyl mesylate).

E.

(1α,2β,3β,4α)-5-[[[3-[(Hexyloxy)methyl]-7-oxabicyclo[2.2.1]hept-2-yl]methyl]thio]pentanoic acid To 200 mg of crude Part D compound (ca. 0.45 mmole) in 80 ml of THF and 20 ml of H$_2$O saturated with argon at 0° C. was added 4.5 ml of a 1M lithium hydroxide solution. The mixture was stirred at 25° C. for 20 hours and concentrated in vacuo. The residue was diluted with 10 ml of H$_2$O and acidified to pH 3 with a saturated aqueous solution of oxalic acid. The aqueous solution was extracted with three 40 ml portions of ether. The combined organic extracts was washed with two 40 ml portions of H$_2$O, dried over anhydrous MgSO$_4$ and with two 40 ml portions of H$_2$O, dried over anhydrous MgSO$_4$ and concentrated. The residue was purified on a CC-7 silica gel column, eluting with a gradient of pentane/ether to yield the title compound.

TLC: silica gel; 7% MeOH in CH$_2$Cl$_2$; R$_f$~0.55.
Anal Calcd for C$_{19}$H$_{34}$O$_4$S: C, 63.64; H, 9.56; S, 8.94. Found: C, 63.41; H, 9.52; S, 8.70.

F.

(1α,2β,3β,4α)-5-[[[3-[(Hexyloxymethyl]-7-oxabicyclo[2.2.1]hept-2-yl]methyl]thio]-N-hydroxy-N-methylpentanamide Following the procedure of Example 1 Part R, the title compound is obtained.

EXAMPLE 2

(1α,2β,3β,4α)-4-[[2-[3-[(Phenoxy)methyl]-7-oxabicyclo[2.2.1]hept-2-yl]ethyl]thio]-N-hydroxy-N-methyl-4-butanamide

A.

(1α,2β,3β,4α)-2-[3-[(Phenoxy)methyl]-7-oxabicyclo[2.2.1]hept-2-yl]ethanol

A solution of 1.44 g (5.66 mmol) of (1β,2β,3β,4α)-2-[3-[(phenoxy)methyl]-7-oxabicyclo[2.2.1]hept-2-yl-acetaldehyde in dry tetrahydrofuran (20 ml) was cooled down to 0° and treated with 173.4 mg (4.57 mmole) of lithium aluminum hydride under argon. The mixture was allowed to warm up to 25° over 1.5 hour and was then treated with 4 ml Na$_2$SO$_4$ and stirred for 30 minutes. The mixture was diluted with 50 ml CH$_2$Cl$_2$, stirred for 30 minutes and filtered. The precipitates were washed with another 50 ml CH$_2$Cl$_2$; the organic solutions were combined and dried over anhydrous MgSO$_4$. The solutions were filtered and stripped to dryness to yield 1.37 g of liquid (after evacuating for 4 hours). The crude product mixture was dissolved in 25 ml CH$_2$Cl$_2$ and flash chromatgraphed on a silica gel column (LPS-1) using ethyl acetate:hexane (1:3), and ethyl acetate:hexane (1:1). The fractions containing the desired product were collected and concentrated to give 1.22 g of the title compound.

B.

(1α,2β,3β,4α)-[2-[3-[(Phenoxy)methyl]-7-oxabicyclo[2.2.1]hept-2-yl]ethyl]thioacetate Triphenylphosphine (2.31 g, 8.72 mmole) was suspended and stirred in dry tetrahydrofuran (37 ml) under N$_2$ at 0°, and treated dropwise over a period of 15 minutes with diisopropylazadicarboxylate (1.8 ml, 8.89 mmole). After 30 minutes the suspension was treated with a solution of 1.12 g (4.37 mmole) of [1α,2β,3β,4α]-2-[3-(hexyloxy)methyl]-7-oxabicyclo[2.2.1]hept-2-yl]ethanol and thiolacetic acid (0.63 ml, 8.81 mmole) in dry tetrahydrofuran (5 ml). The mixture was stirred at 0° for 1 hour, at room temperature for 4 hours and was concentrated to a syrup in vacuo. The syrup was triturated with Et$_2$O:Hexane (1:4, 100 ml) and the precipitates that formed were filtered off and washed with Et$_2$O:Hexane (1:4, 100 ml). The clear filtrate and washings were combined and were concentrated to give 4.64 g of a semi-solid containing the desired product.

The above product mixture was chromatographed (flash) on a silica gel column (LPS-1) eluting the column with Et$_2$O:Hexane (1:9, 4.6 liters). The fractions containing the desired title compound were combined and concentrated to give 1.5 g (100%) of an oil with consistent $^1$H and $^{13}$C spectral data.

C.

(1α,2β,3β,4α)-[2-[3-[(Phenoxy)methyl]-7-oxabicyclo[2.2.1]hept-2-yl]ethanethiol The Part B thioacetate (514 mg, 1.63 mmole) was dissolved in dry tetrahydrofuran (5 ml) and added to a suspension of 75 mg (1.98 mmole) of LAH in dry tetrahydrofuran (5 ml) at 0° under N$_2$. The mixture was stirred at 0° for 1.5 hours and was then quenched cautiously by successive additions of water (0.08 ml), 10% NaOH (0.12 ml) and water (0.24 ml). The mixture was stirred for 30 minutes, diluted with dichloromethane (25 ml) and filtered, washing the solids with CH$_2$Cl$_2$ (35 ml). The clear filtrate and washings were combined, dried (anhydrous MgSO$_4$) and was concentrated to give 396 mg (89.2%) of title thiol compound as a homogeneous (tlc) oil with a consistent $^1$H spectrum.

D.

(1α,2β,3β,4α)-4-[[2-[3-[(Phenoxy)methyl]-7-oxabicyclo[2.2.1]hept-2-yl]ethyl]thio]butanoic acid, methyl ester Part C thiol (500 mg, 5.8 mmole) and 1.0 g of powdered anhydrous K$_2$CO$_3$ were stirred in dry acetone (20 ml) under N$_2$ for a few minutes at room temperature and was treated with a solution of 738 mg (5.4 mmole) of 4-chloromethylbutyrate in dry acetone (5.0 ml). The mixture was stirred at room temperature for 48 hours, diluted with ether (100 ml) and filtered. The filtrate was dried (anhydrous MgSO$_4$), filtered and was concentrated to give an oil (1.47 g) containing the desired product and three minor components (tlc). The mixture was chromatographed (flash) on a silica gel column (LPS-1), eluting with Et$_2$O:Hexane (1:4, 3.5 liters) to give, after drying in vacuo, the title ester as an oil (496 mg, 74%) with consistent analytical, H$^1$-NMR, C$^{13}$-NMR, mass, and IR spectral data.

E.

(1α,2β,3β,4α)-4-[[2-[3-[(Phenoxy)methyl]-7-oxabicyclo[2.2.1]hept-2-yl]ethyl]thio]butanoic acid Following the procedure of Example 1 Part Q except substituting the above Part D ester for the Example 1 Part P ester, the title acid is obtained.

F.

(1α,2β,3β,4α)-4-[[2-[3-[(Phenoxy)methyl]-7-oxabicyclo[2.2.1]hept-2-yl]ethyl]thio]-N-hydroxy-N-methyl-4-butanamide Following the procedure of Example 1 Part R except substituting the above Part E acid for the Example 1 Part Q acid, the title compound is obtained.

EXAMPLE 3

(1α,2β,3β,4α)-[[5-[[3-[(Hexyloxy)methyl]-7-oxabicyclo[2.2.1]hept-2-yl]-methyl]oxy]-N-hydroxy-N-methyl-pentanamide

A.

(1α,2β,3β,4α)-Cis-exo-2-hydroxymethyl-3-benzyloxymethyl-7-oxabicyclo[2.2.1]heptane To a suspension of 3.08 g of ether-washed sodium hydride (70 mmole, 50% oil dispersion) in 100 ml of dry DMF was added with stirring at 0° C. a solution of 10.0 g Example 1A diol (64 mmole) in 30 ml of DMF over a period of 15 minutes. The mixture was stirred for 30 minutes at 0° C., 20 minutes at 25° C., cooled to 0° C. and 12.0 g of benzyl bromide (70 mmole) was added dropwise. After stirring at 25° C. for 2 hours, the reaction was quenched with an aqueous ammonium chloride solution, extracted with ether, dried over anhydrous MgSO$_4$ and concentrated to a residue.

Purification of the residue was done on a silica gel column, eluting with 10–20% ethyl acetate in hexane to give 11.8 g of the title monobenzylether.

B.

(1α,2β,3β,4α)-5-[[[3-Benzyloxymethyl]-7-oxabicyclo[2.2.1]hept-2-yl]methyl]oxy]pentanol, [[(1,1-dimethyl)ethyl]dimethyl]silyl ether To a mixture of 6.73 g powdered potassium hydroxide (121 mmole) in 20 ml of dry xylene was added a solution of 3.0 g of title A alcohol (12.1 mmole) in 10 ml of xylene. The mixture was heated to reflux and 15 ml of xylene was distilled off.

To the remaining solution was added a solution of 6.18 g of 5-tert-butyldimethylsilyloxy n-pentylmesylate in 10 ml of xylene. The resulting mixture was refluxed for 1 hour, cooled to 25° C. and diluted with 300 ml of ether. The ethereal solution was washed with two 50 ml portions of water, dried over anhydrous MgSO$_4$ and concentrated.

The residue was purified on a silica gel column, eluting with 20% ether in hexane to give 4.0 g of title compound as a yellow oil.

C.
(1α,2β,3β,4α)-5-[[[3-Benzyloxymethyl-7-oxabicyclo[2.2.1]hept-2-yl]methyl]oxypentanol To 536.5 mg of title B compound (1.19 mmole) in 2 ml of THF at 0° C. was added 755.4 mg of tetra-n-butylammonium fluoride. The mixture was stirred at 0° C. for 2 hours and at 25° C. for 1 hour, then diluted with 50 ml of ether. The ethereal solution was washed with two 10 ml portions of $H_2O$, 10 ml of brine, dried over anhydrous $MgSO_4$ and concentrated to give crude title alcohol as an oil. This was used without further purification.

D.
(1α,2β,3β,4α)-5-[[[3-Benzyloxymethyl-7-oxabicyclo[2.2.1]hept-2-yl]methyl]oxy]pentanoic acid,
and

E.
(1α,2β,3β,4α)-5-[[3-Benzyloxymethyl-7-oxabicyclo[2.2.1]hept-2-yl]methyl]oxy]pentanoic acid, methyl ester To crude title C alcohol in 10 ml of acetone at 0° C. was added dropwise a solution of 2.67M Jones reagent until the reaction mixture remained brown. The mixture was stirred for an additional 30 minutes at 0° C., quenched with isopropanol and diluted with 200 ml of ether. It was washed with 100 ml of saturated $NaHCO_3$ solution. The aqueous layer was acidified with concentrated HCl, saturated with solid NaCl and extracted with five 50 ml portions of $CH_2Cl_2$, dried over anhydrous $MgSO_4$ and concentrated to give 260 mg of title D acid, as an oil.

The above acid, dissolved in 10 ml of ether, was treated with an ethereal solution of diazomethane to give 260 mg of title E ester.

F.
(1α,2β,3β,4α)-5-[[[3-Hydroxymethyl-7-oxabicyclo[2.2.1]hept-2-yl]methyl]oxy]pentanoic acid, methyl ester A mixture of 260 mg title E ester (0.71 mmole) and 130 mg of 10% palladium over carbon in 5 ml of ethylacetate was shaken in a Parr bottle under 40 lbs of hydrogen pressure, at 25° C. for 18 hours. The reaction mixture was filtered through a bed of Celite and the filtrate was concentratred to give 200 mg of title G alcohol as an oil.

G.
(1α,2β,3β,4α)-5-[[[3-[(Hexyloxy)methyl]-7-oxabicyclo[2.2.1]hept-2-yl]methyl]oxy]pentanoic acid, hexyl ester To a solution of 504 mg of powdered potassium hydroxide (8.4 mmole) in 40 ml of dry xylene was added a solution of 217 mg of title F alcohol (0.84 mmole) in 40 ml of xylene. The mixture was heated to reflux and 40 ml of xylene was distilled off. To the remaining solution was added 1.5 g of hexyl mesylate (8.4 mmole). The mixture was refluxed for 3 hours, cooled to 25° C., diluted with 200 ml of ether and washed with two 50 ml portions of $H_2O$. The organic layer was dried over anhydrous $MgSO_4$ and concentrated. The residue was purified on a silica gel column, eluting with 20% EtOAc in hexanes to give 200 mg of title oil (contaminated with some hexyl mesylate).

H.
(1α,2β,3β,4α)-5-[[[3-[(Hexyloxy)methyl]-7-oxabicyclo[2.2.1]hept-2-yl]methyl]oxy]pentanoic acid To 200 mg of crude Part G ester compound (ca. 0.46 mmole) in 80 ml of THF and 20 ml of $H_2O$ at 0° C. was added 4.6 ml of 1M lithium hydroxide solution. The mixture was stirred at 25° C. for 20 hours then concentrated. The residue was diluted with 10 ml of $H_2O$ and acidified with a saturated aqueous oxalic acid solution to pH 3. The aqueous solution was extracted with three 40 ml portions of ether. The combined organic layer was washed with two 40 ml portions of $H_2O$, dried over anhydrous $MgSO_4$ and concentrated. The residue was purified on a CC-7 silica gel column, eluting with a gradient of pentane/ether to yield 155 mg of title compound as a clear oil.

TLC: silica gel; 7% MeOH in $CH_2Cl_2$; $R_f \sim 0.4$. Anal Calcd for $C_{19}H_{34}O_5$: C, 66.63; H, 10.00. Found: C, 66.75; H, 9.82.

I.
(1α,2β,3β,4α)-5-[[[3-[(Hexyloxy)methyl]-7-oxabicyclo[2.2.1]hept-2-yl]methyl]oxy]-N-hydroxy-N-methylpentanamide Following the procedure of Example 1 Part R except substituting the Part I acid for the Example 1 Part Q acid, the title compound is obtained.

EXAMPLE 4
(1α,2β,3β,4α)-5-[[[3-[(Hexylthio)methyl]-7-oxabicyclo[2.2.1]hept-2-yl]methyl]oxy]-N-hydroxy-N-methylpentanamide

A.
(1α,2β,3β,4α)-5-[[3-(p-Toluenesulfonyloxymethyl)-7-oxabicyclo[2.2.1]hept-2-yl]methyl]oxy]pentanoic acid, methyl ester To a solution of 544 mg (2.0 mmol) of (1α,2β,3β,4α)-5-[[(3-(hydroxymethyl)-7-oxabicyclo[2.2.1]hept-2-yl]methyl]oxy]pentanoic acid, methyl ester, prepared as described in Example 1 Part O, in 4 ml of dry pyridine is added 420 mg (2.2 mmol) of tosyl chloride. The mixture is stirred at room temperature under an argon atmosphere for 10 hours. The reaction mixture is diluted with 300 ml of ether, and washed with 1N aqueous HCl solution (3×100 ml). The ether layer is dried over anhydrous magnesium sulfate and concentrated in vacuo. Purification is effected by flash chromatography on 30 g of silica gel 60 using 50% hexane in ether as eluant to give 615 mg of title compound.

B.
(1α,2β,3β,4α)-5[[[3-[(Hexylthio)methyl]-7-oxabicyclo[2.2.1]hept-2-yl]methyl]oxy]pentanoic acid, methyl ester To a solution of 132 mg (1.17 mmol) of potassium t-butoxide in 10 ml of dry THF under argon is added 378 mg (3.21 mmol) of 1-hexanethiol. To this mixture is added a solution of 425 mg (1.0 mmol) of Part A tosylate in 5 ml of THF. The reaction mixture is stirred at room temperature under argon for 2.5 hours and then heated to reflux for 5.5 hours. The cooled reaction is diluted with 300 ml of ether and poured into 100 ml of saturated $NaHCO_3$ solution. The aqueous layer is extracted with ether (2×100 ml). The combined ether extracts (500 ml) are washed with 0.5N aqueous sodium hydroxide (2×100 ml), brine (100 ml), and then dried (MgSO$_4$), filtered and concentrated in vacuo to give 675 g of crude oil. Purification is effected by chromatography on 25.2 g of silica gel 60 using 5:1 pet ether:ether as eluant to give 300 mg of title product as an oil.

C.
(1α,2β,3β,4α)-5-[[[3-[(Hexylthio)methyl]-7-oxabicyclo[2.2.1]hept-2-yl]methyl]oxy]pentanoic acid Following the procedure of Example 1 Part Q except substituting the above Part B ester for the Example 1 Part P ester, the title compound is obtained.

D.
(1α,2β,3β,4α)-5-[[[3-[(Hexylthio)methyl]-7-oxabicyclo[2.2.1]hept-2-yl]methyl]oxy]-N-hydroxy-N-methylpentanamide Following the procedure of Example 1 Part R except substituting the above Part C acid for the Example 1 Part Q acid, the title compound is obtained.

EXAMPLE 5

(1α,2β,3β,4α)-5-[[[3-[(Hexylthio)methyl]-7-oxabicyclo[2.2.1]hept-2-yl]methyl]thio]-N-hydroxy-N-methylpentanamide

A.
(1α,2β,3β,4α)-5-[[3-(p-Toluenesulfonyloxymethyl)-7-oxabicyclo[2.2.1]hept-2-yl]methyl]thio]pentanoic acid, methyl ester To a solution of 576 mg (2.0 mmol) of (1α,2β,3β,4α)-5-[[[3-hydroxymethyl-7-oxabicyclo[2.2.1]hept-2-yl]methyl]thio]pentanoic acid, methyl and ethyl esters prepared as described in Example 1A Part C in 4 ml of dry pyridine is added 420 mg (2.2 mmol) of tosyl chloride. The mixture is stirred at room temperature under an argon atmosphere for 10 hours. The reaction mixture is diluted with 300 ml of ether, washed with 1N aqueous HCl solution (3×100 ml), and 0.5N aqueous NaOH solution (3×100 ml). The ether layer is dried over anhydrous magnesium sulfate and concentrated in vacuo. Purification is effected by flash chromatography on 30 g of silica gel 60 using 50% hexane in ether as eluant to give 860 mg of title compound.

B.
(1α,2β,3β,4α)-5-[[[3-[(Hexylthio)methyl]-7-oxabicyclo[2.2.1]hept-2-yl]methyl]thio]pentanoic acid, hexyl ester To a solution of 132 mg (1.17 mmol) of potassium t-butoxide in 10 ml of dry THF under argon is added 378 mg (3.21 mmol) of 1-hexanethiol. To this mixture is added a solution of 442 mg (1.0 mmol) of Part A tosylate in 5 ml of THF. The reaction mixture is stirred at room temperature under argon for 2.5 hours and then heated to reflux for 5.5 hours. The cooled reaction is diluted with 300 ml of ether and poured into 100 ml of saturated NaHCO$_3$ solution. The aqueous layer is extracted with ether (2×100 ml). The combined ether extracts (500 ml) are washed with 0.5N aqueous sodium hydroxide (2×100 ml), brine (100 ml), and then dried (MgSO$_4$), filtered and concentrated in vacuo to give 690 g of crude oil. Purification is effected by chromatography on 25.2 g of silica gel 60 using 5:1 pet ether:ether as eluant to give 310 mg of title product as an oil.

C.
(1α,2β,3β,4α)-5-[[[3-[(Hexylthio)methyl]-7-oxabicyclo[2.2.1]hept-2-yl]methyl]thio]pentanoic acid Following the procedure of Example 1 except substituting the above Part B ester for the Example 1 Part P ester, the title compound is obtained.

D.
(1α,2β,3β,4α)-5-[[[3-(Hexylthio)methyl]-7-oxabicyclo[2.2.1]hept-2-yl]methyl]thio]-N-hydroxy-N-methylpentanamide Following the procedure of Example 1 Part R except substituting the above Part C acid for the Example 1 Part Q acid, the title compound is obtained.

EXAMPLE 6

(1α,2β,3β,4α)-5-[[[3-[(Hexyloxy)methyl]-7-oxabicyclo[2.2.1]hept-2-yl]ethyl]thio]-N-hydroxy-N-methyl-5-pentanamide

A.
(1α,2β,3β,4α)-cis-exo-3-Isopropyloxycarbonyloxymethyl-2-hydroxymethyl-7-oxabicyclo[2.2.1]heptane To a suspension of 11.4 g of lithium aluminum hydride (300 mmole) in 400 ml of dry THF at 0° C. was added dropwise a solution of 32 g (1α,2β,3β,4α)-cis-exo-[7-oxabicyclo[2.2.1]hept-2-ylα-2,3-dicarboxylic acid anhydride (mesoanhydride) (190 mmole) in 400 ml of dry THF over a period of 1 hour. The reaction mixture was stirred at 25° C. for 18 hours, cooled to 0° C. and quenched by slow addition of a saturated Na$_2$SO$_4$ solution, and filtered. The solid was washed with three 100 ml portions of CH$_2$Cl$_2$. The combined organic layer was dried over MgSO$_4$ and concentrated to give 32 g of (1α,2β,3β,4α)-cis-exo-7-oxabicyclo[2.2.1]heptane-2,3-dimethanol (meso-diol) as a colorless solid.

To a solution of 10 g (63.2 mmole) of meso-diol in 40 ml dry THF at 0° C. was added with stirring 55 ml of a 12.5% by weight solution of phosgene in toluene (63.2 mmole) dropwise over a period of 30 minutes. Argon was then bubbled through the reaction mixture for 15 minutes. The mixture was concentrated to give a crude oil of (1α,2β,3β,4α)-cis-exo-3-chlorocarbonyloxy-2-hydroxymethyl-7-oxabicyclo[2.2.1]heptane.

This oil was dissolved in 30 ml of dry CH$_2$Cl$_2$ and cooled to −50° C. To this solution was added dropwise a solution of 10 ml pyridine in 10 ml CH$_2$Cl$_2$. It was stirred for 10 minutes and quenched with H$_2$O. The mixture was extracted thoroughly with CH$_2$Cl$_2$. The organic extract was dried over MgSO$_4$ and concentrated to give (1α,2β,3β,4α)-7-oxabicylo[2.2.1]heptane 2,3-dimethanol carbonate (cyclic carbonate) as a crystalline solid (10.7 g).

A mixture of 10.7 g of (1α,2β,3β,4α)-cis-exo-7-oxabicyclo[2.2.1]heptane 2,3-dimethanol carbonate (cyclic carbonate) (58.1 mmole) in 100 ml isopropanol was refluxed for 24 hours. Excess isoproponol was removed under reduced pressure to give 14.4 g title A compound (hydroxycarbonate) as a viscous oil.

B.
(1α,2β,3β,4α)-cis-exo-3-Isopropyloxycarbonyloxymethyl-2-p-toluenesulfonyloxymethyl-7-oxabicyclo[2.2.1]heptane To a solution of 19.7 g of title A alcohol (80 mmole) in 30 ml CH$_2$Cl$_2$ and 12.8 ml pyridine (160 mmole, 2 eq.) was added 18.5 g p-toluene-sulfonyl chloride (96 mmole). The mixture was stirred at 25° C. for 36 hours then diluted with 200 ml ether, and washed with 100 ml brine.

The organic layer was dried over MgSO$_4$ and concentrated to give 32.8 g of title crude tosylate as an oil.

C.
(1α,2β,3β,4α)-cis-exo-3-Isopropyloxycarbonyloxymethyl-2-cyanomethyl-7-oxabicyclo[2.2.1]heptane To a solution of 24.0 title B crude tosylate (60 mmole) in 20 ml DMSO was added with stirring 6.0 g powdered sodium cyanide (120 mmole). The mixture was heated at 90°–95° C. for 1.5 hours under an argon atmosphre. The cooled mixture was diluted with 50 ml water and extracted with five 100 ml portions of ether. The ethereal extracts were dried over anhydrous MgSO$_4$ and filtered through a bed of Florosil ®. The filtrate was concentrated, and the residue was recrystallized with ether/hexanes to give 8.4 g of title cyanocarbonate as a light yellow crystalline solid.

D.
(1α,2β,3β,4α)-cis-exo-3-Hydroxymethyl-2-cyanomethyl-7-oxabicyclo[2.2.1]heptane To 8.4 g of title C cyanocarbonate (33.2 mmole) was added 75 ml of a 1% solution of potassium carbonate ion methanol-water (2:1). The reaction mixture was stirred at 25° C. for 6 hours, then acidified with 2N HCl solution, saturated with sodium chloride and extracted with six 100 ml portions of CH$_2$Cl$_2$. The combined organic layer was dried over anhydrous MgSO$_4$ and concentrated to give 5.5 g of crude title cyanoalcohol as a light yellow oil.

E.
(1α,2β,3β,4α)-cis-exo-3-t-Butyldimethylsilyloxymethyl-2-cyanomethyl-7-oxabicyclo[2.2.1]heptane To a solution of 5.0 g title D alcohol (30 mmole) in 50 ml of dry CH$_2$Cl$_2$ and 10 ml of triethylamine (70 mmole, 3.3 eq.) at 0° C. was added with stirring 490 mg 4-dimethylaminopyridine (4 mmole) and 5.28 g t-butyldimethylsilyl chloride (35 mmole). The reaction mixture was slowly warmed to 25° C. and stirred for 18 hours, then diluted with 200 ml ether and filtered through a small bed of anhydrous MgSO$_4$. The filtrate was concentrated. Purification was done on a silica gel column, eluting with 15% ethyl acetate in hexanes to give 10.25 g of title silyl ether as a light yellow oil.

F.
(1α,2β,3β,4α)-cis-exo-3-t-Butyldimethylsilyloxymethyl-2-formylmethyl-7-oxabicyclo[2.2.1]heptane To a solution of 10.0 g of title E silyl ether (26.2 mmole) in 30 ml of dry toluene at −78° C. under an argon atmosphere was added dropwise 25 ml of a 25% by weight solution of diisobutylaluminum hydride (44 mmole) in toluene. The mixture was stirred at −78° C. for 4 hours, quenched at −78° C. with a saturated solution of ammonium chloride, warmed to 0° C., acidified with 1N HCl solution, extracted with three 100 ml portions of CH$_2$Cl$_2$, dried over anhydrous MgSO$_4$ and concentrated to give 9.3 g of crude title aldehyde.

G.
(1α,2β,3β,4α)-cis-exo-2-[3-t-Butyldimethylsilyloxymethyl-7-oxabicyclo[2.2.1]hept-2-yl]ethanol To 9.3 crude title F aldehyde (32.7 mmole) in 30 ml of dry THF at 0° C. under an argon atmosphere was added portionwise 1.0 g lithium aluminum hydride (26.0 mmole) with stirring. The reaction mixture was stirred while being warmed to 25° C. over a period of 1 hour, quenched by slow addition of a saturated sodium sulfate at 0° C., dried over anhydrous MgSO$_4$ and filtered. The solid was washed with CH$_2$Cl$_2$. The combined filtrate was concentrated to give a crude oil. This oil was purified on a silica gel column, eluting with 30% EtOAc in hexanes to give 8.55 g title alcohol as a colorless oil.

H.
(1α,2β,3β,4α)-2-[2-[3-t-Butyldimethylsilyloxymethyl-7-oxabicyclo[2.2.1]hept-2-yl]ethyl]thioacetate To a solution of 5.25 g triphenylphosphine (20 mmole) in 60 ml dry THF at 0° C. was added dropwise 4.16 g diisopropylazodicarboxylate (20 mmole) over a period of 15 minutes. The mixture was stirred at 0° C. for 20 minutes, and a solution of 2.6 title G alcohol (10 mmole) and 1.45 ml of thiolacetic acid (20 mmole) in 10 ml dry THF was added dropwise. The reaction mixture was stirred at 0° C. for 1 hour, 25° C. for 3 hours, and was concentrated. The residue was triturated with ether/hexane, filtered, and the filtrate was concentrated and purified on a silica gel column, eluting with 10% EtOAc in hexane to give 2.3 g title thioacetate as a light yellow oil.

I.
(1α,2β,3β,4α)-2-[2-[3-Hydroxymethyl-7-oxabicyclo[2.2.1]hept-2-yl]ethyl]thioacetate To a solution of 2.3 g title H thioacetate (6.7 mmole) in 20 ml dry THF at 0° C. was added 2.23 g of tetra-n-butylammoniumfluoride trihydrate (7.07 mmole) in 5 ml dry THF. The mixture was warmed at 25° C. and stirred for 18 hours, diluted with 100 ml ether, washed with 30 ml of a saturated NaHCO$_3$ solution, dried over anhydrous MgSO$_4$ and concentrated to give a crude oil.

Purification was done on a silica gel column, eluting with 20% EtOAc in hexanes and 50% EtOAc in hexanes to give 1.22 g of title alcohol-thioacetate as a colorless oil.

J.
(1α,2β,3β,4α)-2-[3-Hydroxymethyl-7-oxabicyclo[2.2.1]hept-2-yl]ethanethiol To a slurry of 200 mg lithium aluminum hydride (5.27 mmole) in 20 ml dry THF at 0° C. was added a solution of 1.22 g title I thioacetate (5.3 mmole) in 5 ml THF dropwise under an argon atmosphere. The reaction mixture was stirred at 0° C. for 1 hour, quenched with a saturated sodium sulfate solution, dried with anhydrous MgSO$_4$, and was filtered. The filtrate was concentrated to give 900 mg of the title thiol as a colorless oil.

K.
[1α,2β,3β,4α]-5-[[2-[3-Hydroxymethyl-7-oxabicyclo[2.2.1]hept-2-yl]ethyl]thio]pentanoic acid, ethyl ester To a slurry of 1.38 g of dried and powdered sodium hydride (5.75 mmole) in 20 ml dry tetrahydrofuran at 0° C. is added a solution of 900 mg title J thiol (4.8 mmole) in 5 ml THF followed by 1.75 ml of ethyl-5-bromovalerate (11.05 mmole, (2.3 eq.). The reaction mixture is stirred at 0° C. for 10 hours, diluted with 100 ml ether and filtered through a pad of anhydrous MgSO$_4$. The filtrate is then concentrated. The residue is purified on a silica gel column, eluting with 20% EtOAc in hexanes and 50% EtOAc in hexanes to give 1.22 g of title alcohol as a colorless oil.

L.
(1α,2β,3β,4α)-5-[[2-[3-[(Hexyloxy)methyl]-7-oxabicyclo[2.2.1]hept-2-yl]ethyl]thio]pentanoic acid, hexyl ester Following the procedure of Example 3 Part G except substituting the above Part K alcohol for the Example 3 Part F alcohol, the title compound is obtained.

M.
(1α,2β,3β,4α)-5-[[2-[3-[(Hexyloxy)methyl]-7-oxabicyclo[2.2.1]hept-2-yl]ethyl]thio]pentanoic acid Following the procedure of Example 1 Part Q except substituting the Part L hexyl ester for the Example 1 Part P ester, the title compound is obtained.

N.
(1α,2β,3β,4α)-5-[[[(3-Hexyloxy)methyl]-7-oxabicyclo[2.2.1]hept-2-yl]ethyl]thio]-N-hydroxy-N-methylpentanamide Following the procedure of Example 1 Part R except substituting the above Part M acid for the Example 1 Part Q acid, the title compound is obtained.

EXAMPLE 7
[1R-(1α,2β,3β,4α)]-4-[2-[3-[(Hexyloxy)methyl]-7-oxabicyclo[2.2.1]hept-2-yl]ethoxy]-N-hydroxy-N-methylbutanamide

A.
[1R-(1α,2β,3β,4α)]-2-(Benzyloxy)methyl-3-cyanomethyl-7-oxabicyclo]2.2.1]heptane To a slurry of 1.1 g of sodium hydride (21 mmole, 50% oil dispersion) in 25 ml of dry DMF at 0° C. was added a solution of 3.34 g of Example 1 Part G cyanoalcohol (20 mmole) in 10 ml of DMF over a period of 10 minutes. After stirring for an additional b 15 minutes, 3.6 g of benzyl bromide was added dropwise. The reaction mixture was stirred for 30 minutes at 0° C. and 3 hours at 25° C. then quenched with a saturated ammonium chloride solution, and diluted with ether. The organic layer was washed with brine. The combined aqueous layer was re-extracted with ether. The combined organic layer was dried over anhydrous MgSO4 and concentrated to leave an oil. The crude oil was chromatographed on a silica gel column, eluting with 10–20% ethyl acetate in hexanes to give 4.43 g of the title A benzyl ether.

B.
[1R-(1α,2β,3β,4α)]-2-[[3-Benzyloxy)methyl]-7-oxabicyclo[2.2.1]hept-2-yl]acetaldehyde and

C.
[1R-(1α,2β,3β,4α)]-2-[[3-(Benzyloxy)methyl]-7-oxabicyclo[2.2.1]hept-2-yl]ethanol To a solution of 4.43 g of title A nitrile (17.24 mmole) in 20 ml of dry toluene at −78° C. was added dropwise 20 ml of a 25% by weight solution of diisobutylaluminum hydride in toluene (35 mmole). After stirring at −78° C. for 4 hours the reaction was quenched with a saturated ammonium chloride solution. The mixture was warmed to 25° C. and 50 ml of a 1N aqueous hydrochloric acid solution was added. The organic layer was separated and the aqueous layer was extracted several times with ether. The combined organic extract was dried over anhydrous MgSO4 and concentrated to give 4.55 g of crude title B aldehyde.

To the above crude title B aldehyde (17.24 mmole) in 30 ml of dry THF at 0° C. was added 380 mg of lithium aluminum hydride (10 mmole) portionwise. After stirring while warming to 25° C. over a period of 1 hour, the reaction was quenched with a saturated sodium sulfate solution. Solid anhydrous MgSO4 was added and the mixture was filtered. The filtrate was concentrated to give 4.25 g of title C alcohol as a colorless oil.

D.
[1R-(1α,2β,3β,4α)]-4-[2-[[3-(Benzyloxy)methyl]-7-oxabicyclo[2.2.1]hept-2-yl]ethoxy]butanol, t-butyldimethylsilyl ether To a mixture of 4.5 g of powdered potassium hydroxide (82.6 mmole) in 20 ml of dry xylene was added a solution of 2.0 g of title C alcohol (8.26 mmole) in 10 ml of xylene. The mixture was heated to reflux and 15 ml of xylene was distilled off. To the remaining solution was added a solution of 4.0 g of 4-tert-butyldimethylsilyloxy n-butylmesylate in 10 ml of xylene. The resulting mixture was refluxed for 1 hour, cooled to 25° C. and diluted with 300 ml of ether. The ethereal solution was washed with two 50 ml portions of water, dried over anhydrous MgSO4 and concentrated. The residue was purified on a silica gel column, eluting with 20% ether in hexanes to give 1.4 g of title D compound as a yellow oil.

E.
[1R-(1α,2β,3β,4α)]-4-[2-[[3-(Benzyloxy)methyl]-7-oxabicyclo[2.2.1]hept-2-yl]ethoxybutanol To 1.2 g of title D compound (2.68 mmole) in 5 ml of THF at 0° C. was added 1.1 g of tetra-n-butylammonium fluoride (3.46 mmole). The mixture was stirred at 0° C. for 1 hour and at 25° C. for 1 hour and was diluted with 50 ml of ether. The ethereal solution was washed with two 10 ml portions of H2O, 10 ml of brine, dried over anhydrous MgSO4 and concentrated to give crude title E alcohol as an oil. This was used without purification.

F.
[1R-(1α,2β,3β,4α)]-4-[[2-[3-(Benzyloxy)methyl]-7-oxabicyclo[2.2.1]hept-2-yl]ethoxy]butanoic acid and

G.
[1R-(1α,2β,3β,4α)]-4-[2-[[3-(Benzyloxy)methyl]-7-oxabicyclo[2.2.1]hept-2-yl]ethoxy]butanoic acid, methyl ester To crude title E alcohol in 30 ml of acetone at 0° C. was added dropwise a solution of 2.6M Jones' reagent until the reaction mixture remained brown in color. The mixture was stirred for an additional 30 minutes at 0° C., quenched with isopropanol and diluted with 200 ml of ether. Anhydrous sodium acetate along with anhydrous magnesium sulfate was added. The mixture was stirred for 15 minutes at 25° C. and filtered through a bed of Florosil ®. The filtrates were concentrated. The residue was treated with 200 ml of a saturated NaHCO3 solution and extracted with two 50 ml portions of ether. The aqueous layer was acidified with concentrated HCl, saturated with solid NaCl and extracted with five 100 ml portions of CH2Cl2, dried over anhydrous MgSO4 and concentrated to give title F acid as an oil.

The above title F acid, dissolved in 30 ml of ether, was treated with an ethereal solution of diazomethane to give an oil which was purified on a silica gel column, eluting with 20% EtOAc in hexanes to yield 500 mg of pure title G ester.

H.
[1R-(1α,2β,3β,4α)]-4-[[2-[3-(Hydroxymethyl)]-7-oxabicyclo[2.2.1]hept-2-yl]ethoxy]butanoic acid, methyl ester A mixture of 500 mg of title G ester (1.38 mmole), 250 mg of 10% palladium over carbon in 10 ml of ethyl acetate and 1 ml of glacial acetic acid was shaken in a Parr bottle under 40 lbs. of hydrogen pressure at 25° C. for 18 hours. The mixture was filtered through a bed of Celite and concentrated to give 242 mg of title H alcohol as an oil.

J.
[1R-(1α,2β,3β,4α)]-4-[2-[3-[(Hexyloxy)methyl]-7-oxabicyclo[2.2.1]hept-2-yl]ethoxy]butanoic acid, hexyl ester Following the procedure of Example 3 Part G except substituting the above Part H alcohol for the Example 3 Part F alcohol, the title compound is obtained.

K.
[1R-(1α,2β,3β,4α)]-4-[2-[3-[(Hexyloxy)methyl]-7-oxabicyclo[2.2.1]hept-2-yl]ethoxy]butanoic acid Following the procedure of Example 1 Part Q except substituting the Part J hexyl ester for the Example 1 Part P hexyl ester, the title compound is obtained.

L.
[1R-(1α,2β,3β,4α)]-4-[2-[3-[(Hexyloxy)methyl]-7-oxabicyclo[2.2.1]hept-2-yl]ethoxy]-N-hydroxy-N-methylbutanamide Following the procedure of Example 1 Part R except substituting the above Part K acid for the Example 1 Part Q acid, the title compound is obtained.

EXAMPLE 9
(1α,2β,3β,4α)-5-[[2-[3-[(Hexylthio)methyl]-7-oxabicyclo[2.2.1]hept-2-yl]ethyl]thio]-N-hydroxy-N-methylpentanamide Following the procedure of Example 5 except substituting (1α,2β,3β,4α)-5-[[2-[3-hydroxymethyl-7-oxabicyclo[2.2.1]hept-2-yl]ethyl]thio]pentanoic acid, methyl ester (prepared in Example 6, Part K) for the Example 1A Part C alcohol, the title compound is obtained.

EXAMPLE 10
(1α,2β,3β,4α)-4-[[2-[3-[(Hexylthio)methyl]-7-oxabicyclo[2.2.1]hept-2-yl]ethoxy]-N-hydroxy-N-methylbutanamide Following the procedure of Example 4 except substituting (1α,2β,3β,4α)-4-[2-[3-hydroxymethyl-7-oxabicyclo[2.2.1]hept-2-yl]ethoxy]butanoic acid, methyl ester (prepared in Example 7, Part I) for the Example 3 Part F alcohol, the title compound is obtained.

EXAMPLE 11
(1α,2β,3β,4α)-5-[[3-[2-Hexyloxy)ethyl]-7-oxabicyclo[2.2.1]hept-2-yl]methoxy]-N-hydroxy-N-methylpentanamide

A.
(1α,2β,3β,4α)-5-[[(3-Formyl)-7-oxabicyclo[2.2.1]hept-2-yl]methoxy]pentanoic acid, methyl ester To 5.44 g of (1α,2β,3β,4α)-5-[[3-(hydroxymethyl)-7-oxabicyclo[2.2.1]hept-2-yl]methoxy]pentanoic acid, methyl ester prepared as described in Example 3, Part F (20 mmole) in 65 ml of dry $CH_2Cl_2$ at 25° C. is added 13.0 g Celite, 1.7 g NaOAc (6.15 mmole, 30 mole %) and 12.94 g pyridinium chlorochromate (60 mmole, 3 eq.). The mixture is stirred at 25° C. for 2 hours, diluted with 100 ml ether and filtered through a bed of Florosil ®. The filtrate is concentrated to give 5.25 g of title aldehyde as a clear oil which is used in the next reaction without further purification.

B.
(1α,2β,3β,4α)-5-[[3-(2-Oxo)ethyl]-7-oxabicyclo[2.2.1]hept-2-yl]methoxy]pentanoic acid, methyl ester Into a dry 100 ml round bottom 3-necked flask containing a stir bar is added dried methoxymethyltriphenylphosphonium chloride $((C_6H_5)_3P^+-CH_2OCH_3Cl^-)$ (3.25 g, 9.54 mmole) and 30 ml distilled toluene (stored over molecular sieves). The resulting suspension is stirred in an ice-bath, under argon until cold and a 1.4M solution of 5.73 ml (8.01 mmol) of potassium t-amylate in toluene is added dropwise. A bright red solution is formed which is stirred at 0° C. for an additional 35 minutes. Thereafter, a solution of 1.04 g (3.84 mmol) of (1α,1β,3β,4α)-5-[[(3-formyl)-7-oxabicyclo[2.2.1]hept-2-yl]methoxy]pentanoic acid, methyl ester in 10 ml toluene is added by means of a dropping funnel over a 35 minute period with the ice-bath still in place. The reaction is then quenched by addition of 2.3 g (39 mmol) of acetic acid in 5 ml ether. The reaction mixture is immediately poured into 200 ml of saturated $NH_4Cl$, and extracted with ether (4×200 ml). The combined ether phases is washed with a saturated NaCl solution, and dried ($MgSO_4$) and concentrated to yield an oil in a white crystalline solid (phosphine oxide). The white solid is removed after trituration with EtOAc and the mother liquor is purified by chromatography on an LPS-1 silica column to obtain the enol-ether. The enol-ether is dissolved in 20 ml of THF and then treated with 10 ml of a 20% aqueous trifluoroacetic acid solution. After 1 hour at room temperature, sodium bicarbonate is carefully added. The mixture is then extracted several times with methylene chloride. The combined methylene chloride extract is dried over anhydrous magnesium sulfate and concentrated under reduced pressure. Chromatography on a LPS-1 silica gel column and elution with 15–30% ethylacetate in hexane gives 980 mg of title B aldehyde.

C.
(1α,2β,3β,4α)-5-[[3-[2-(Hydroxy)ethyl]-7-oxabicyclo[2.2.1]hept-2-yl]methoxy]pentanoic acid ester The aldehyde (980 g, 3.45 mmol) from part B in methanol (50 ml) is treated with $NaBH_4$ (0.19 g, 5 mmol) in an argon atmosphere at 0° C. After stirring at 0° C. for 1 hour, the reaction is quenched by addition of 2N HCl (to pH 2). The methanol is removed in vacuo and the reaction mixture is taken up in ether. The ether solution is washed with saturated KHCO$_3$, saturated NaCl and dried (MgSO$_4$, anhydrous). The ether is evaporated to yield the title C compound.

D.

(1α,2β,3β,4α)-5-[[3-[2-(Hexyloxy)ethyl]-7-oxabicyclo[2.2.1]hept-2-yl]methoxy]pentanoic acid Following the procedure of Example 1, Part P except substituting the above part C alcohol for the Example 1 Part O alcohol used in Example 1 Part P, the title compound is obtained.

E.

(1α,2β,3β,4α)-5-[[3-[2-(Hexyloxy)ethyl]-7-oxabicyclo[2.2.1]hept-2-yl]methoxy]-N-hydroxy-N-methylpentanamide Following the procedure of Example 1 Part R except substituting the above Part D acid for the Example 1 Part Q acid, the title compound is obtained.

EXAMPLE 12

(1α,2β,3β,4α)-5-[[[3-[2-(Hexyloxy)ethyl]-7-oxabicyclo[2.2.1]hept-2-yl]methyl]thio]N-hydroxy-N-methylpentanamide

A.

(1α,2β,3β,4α)-5-[[[3-[2-(Hexyloxy)ethyl]-7-oxabicyclo[2.2.1]hept-2-yl]methyl]thio]pentanoic acid Following the procedure of Examples 1 Part P except substituting (1α,2β,3β,4α)-5-[[3-(2-hydroxy)ethyl]-7-oxabicyclo-[2.2.1]hept-2-yl]methyl]thio]pentanoic acid, methyl ester (prepared as described in Example 14 Parts A to C) for the alcohol used in Example 1 Part P, the title compound is obtained.

B.

(1α,2β,3β,4α)-5-[[[3-(2-Hexyloxy)ethyl]-7-oxabicyclo[2.2.1]hept-2-yl]methyl]thio]-N-hydroxy-N-methylpentanamide Following the procedure of Example 1 Part R except substituting the above Part A acid for the Example 1 Part Q acid, the title compound is obtained.

EXAMPLE 13

(1α,2β,3β,4α)-5-[[3-[(2-Hexylthio)ethyl]-7-oxabicyclo[2.2.1]hept-2-yl]methoxy]-N-hydroxy-N-methylpentanamide Following the procedure of Example 4 except substituting (1α,2β,3β,4α)-5-[[3-(2-hydroxyethyl)-7-oxabicyclo[2.2.1]hept-2-yl]methoxy]pentanoic acid, methyl ester (prepared as described in Example 11 Part C) for the Example 1 Part O alcohol, the title compound is obtained.

EXAMPLE 14

(1α,2β,3β,4α)-5-[[[3-[2-(Hexylthio)ethyl]-7-oxabicyclo[2.2.1]hept-2-yl]methyl]thio]-N-hydroxy-N-methylpentanamide

A.

(1α,2β,3β,4α)-5-[[[(3-Formyl)-7-oxabicyclo[2.2.1]hept-2-yl]methyl]thio]pentanoic acid, methl ester To a solution of 4 ml of oxalyl chloride (35 mmole) in 10 ml of dry methylene chloride at −60° C. is added dropwise 6.5 ml of dry dimethylsulfoxide (90 mmole) over a period of 15 minutes. After stirring for an additional 30 minutes, a solution of 2.51 g of (1α,2β,3β,4α)-5-[[[3-hydroxymethyl-7-oxabicyclo[2.2.1]hept-2-yl]methyl]thio pentanoic acid, methyl ester (prepared as described for Examples 6K or 12A) (8.7 mmole) in 10 ml of dry methylene chloride is added dropwise over a period of 15 minutes. The mixture is stirred at −60° C. for 30 minutes and then 10 ml of distilled triethylamine (∼70 mmole) is added. The reaction is then warmed to room temperature and water is added. It is then stirred at room temperature for additional 30 minutes, extracted with methylene chloride and washed with a saturated bicarbonate solution. The organic layer is dried over anhydrous magnesium sulfate and concentrated under reduced pressure.

Purification of the crude residue on a LPS-1 silica gel column and elution with 10–30% ethyl acetate in hexane gives 1.72 g of title A aldehyde.

B.

(1α,2β,3β,4α)-5-[[[3-(2-Oxo)ethyl]-7-oxabicyclo[2.2.1]hept-2-yl]methyl]thio]pentanoic acid, methyl ester Into a dry 100 ml round bottom 3-necked flask containing a stir bar is added dried 3.27 g (9.54 mmoles) methoxymethyltriphenylphosphonium chloride (C$_6$H$_5$)$_3$P$^+$—CH$_2$OCH$_3$Cl$^-$) and 30 ml distilled toluene (stored over molecular sieves) under argon. The resulting suspension is stirred in an ice-bath until cold and then a 1.4M solution of 5.73 ml (8.01 mmol) of potassium t-amylate in toluene is added dropwise. A bright red solution forms which is stirred at 0° C. for an additional 35 minutes. Thereafter, a solution of 1.08 g (3.84 mmol) of (1α,2β,3β,4α)-5-[[[(3-formyl)-7-oxabicyclo[2.2.1]hept-2-yl]methyl]thio]pentanoic acid, methyl ester in 10 ml toluene is added by means of a dropping funnel over a 35 minute period with the ice-bath still in place. The reaction is then quenched by addition of 2.3 g (39 mmol) acetic acid in 5 ml ether. The mixture is immediately poured into 200 ml saturated NH$_4$Cl, and extracted with ether (4×200 ml). The combined ether phases are washed with NaCl saturated solution, dried (MgSO$_4$ anhydrous) and concentrated to yield an oil in a white crystalline solid (phosphine oxide). The white solid is triturated with EtOAc, removed by filtration, and the mother liquor is purified by chromatography on an LPS-1 silica column to obtain the enol-ether. The enol ether is dissolved in 20 ml of THF and is then treated with 10 ml of a 20% aqueous trifluoro acetic acid solution. After 1 hour at room temperature, the trifluoroacetic acid is neutralized by addition of solid sodium bicarbonate. The mixture is then extracted with methylene chloride. The methylene chloride extract is dried over anhydrous magnesium sulfate and concentrated under reduced pressure. Chromatography of the crude residue on a LPS-1 silica gel column and elution with 15–30% ethyl acetate in hexane gives 1.02 g of title B aldehyde.

C.

(1α,2β,3β,4α)-5-[[[3-(2-Hydroxyethyl)-7-oxabicyclo[2.2.1]hept-2-yl]methyl]thio]pentanoic acid methyl ester The aldehyde (1.02 g, 3.45 mmol) from part B in methanol (50 ml) is treated with NaBH$_4$ (0.19 g, 5 mmol) in an argon atmosphere at 0° C. After stirring at 0° C. for 1 hour, the reaction is quenched by addition of 2N HCl (to pH 2). The methanol is removed in vacuo and the mixture is taken up in ether. The ether solution is washed with a saturated KHCO$_3$ solution, saturated NaCl solution and dried (MgSO$_4$ anhydrous). The ether is evaporated to yield the title C compound.

D.
(1α,2β,3β,4α)-5-[[[3-[2-(Hexyloxy)ethyl]-7-oxabicyclo[2.2.1]hept-2-yl]methyl]thio]pentanoic acid Following the procedure of Example 1A, Part D except substituting the above part C alcohol for the Example 1A Part C alcohol, the title compound is obtained.

E.
(1α,2β,3β,4α)-5-[[[3-[2-(Hexylthio)methyl]-7-oxabicyclo[2.2.1]hept-2-yl]methyl]thio]-N-hydroxy-N-methylpentanamide Following the procedure of Example 1 Part R except substituting the above Part D acid for Example 1 Part Q acid, the title compound is obtained.

EXAMPLE 15

(1α,2β,3β,4α)-4-[2-[3-[2-(Hexyloxy)ethyl]-7-oxabicyclo[2.2.1]hept-2-yl]ethoxy]-N-hydroxy-N-methylbutanamide A.
(1α,2β,3β,4α)-4-[2-[3-Formyl-7-oxabicyclo2.2.1]hept-2-yl]ethoxy]butanoic acid, methyl ester Following the procedure of Example 11 Part A except substituting (1α,2β,3β,4α)-4-[2-[3-hydroxymethyl-7-oxabicyclo[2.2.1]hept-2-yl]ethoxy]butanoic acid, methyl ester (prepared as described in Example 7 Part H) for the Example 3 Part F alcohol, the title alcohol is obtained.

B.
(1α,2β,3β,4α)-4-[[2-[3-(2-Oxo)ethyl]-7-oxabicyclo[2.2.1]hept-2-yl]ethoxy]butanoic acid, methyl ester Following the procedure of Example 11 Part B except substituting the above Part A aldehyde for the Example 11 Part A aldehyde, the title compound is obtained.

C.
(1α,2β,3β,4α)-4-[2-[[3-(2-Hydroxy)ethyl]-7-oxabicyclo[2.2.1]hept-2-yl]ethoxy]butanoic acid, methyl ester Following the procedure of Example 11 Part C except substituting the above Part B aldehyde for the Example 11 Part B aldehyde, the title compound is obtained. cl D. (1α,2β,3β,4α)-4-[2-[3-[2-(Hexyloxy)ethyl]-7-oxabicyclo[2.2.1]hept-2-yl]ethoxy]butanoic acid Following the procedure of Example 3 Parts G and H except substituting the above Part C alcohol for the Example 3 Part F alcohol used in Example 1 Part G, the title compound is obtained.

E.
(1α,2β,3β,4α)-4-[2-[3-[2-(Hexyloxy)methyl]-7-oxabicyclo[2.2.1]hept-2-yl]ethoxy]-N-hydroxy-N-methylbutanamide Following the procedure of Example 1 Part R except substituting the above Part D acid for the Example 1 Part Q acid, the title compound is obtained.

EXAMPLE 16

(1α,2β,3β,4α)-5-[[2-[3-[2-(Hexyloxy)ethyl]-7-oxabicyclo[2.2.1]hept-2-yl]ethyl]thio]-N-hydroxy-N-methylpentanamide A.
(1α,2β,3β,4α)-5-[[[2-(3-Formyl)-7-oxabicyclo[2.2.1]hept-2-yl]ethyl]thio]pentanoic acid, methyl ester Following the procedure of Example 11 Part A except substituting (1α,2β,3β,4α)-4-[[2-[(hydroxy)methyl-7-oxabicyclo[2.2.1]hept-2-yl]ethyl]thio]pentanoic acid, methyl and ethyl esters (prepared as described in Example 6 Part K) for the Example 3 Part F alcohol, the title compound is obtained.

B.
(1α,2β,3β,4α)-5-[[2-[3-(2-Oxo)ethyl]-7-oxabicyclo[2.2.1]hept-2-yl]ethyl]thio]pentanoic acid, methyl and ethyl esters Following the procedure of Example 11 Part B except substituting the above Part A aldehyde for the Example 11 Part A aldehyde, the title compound is obtained.

C.
(1α,2β,3β,4α)-5-[[2-[3-[(2-Hydroxy)ethyl]-7-oxabicyclo[2.2.1]hept-2-yl]ethyl]thio]pentanoic acid, methyl and ethyl esters Following the procedure of Example 11 Part C except substituting the above Part B aldehyde for the Example 11 Part B aldehyde, the title compound is obtained.

D.
(1α,2β,3β,4α)-5-[[2-[3-[2-(Hexyloxy)ethyl]-7-oxabicyclo[2.2.1]hept-2-yl]ethyl]thio]pentanoic acid Following the procedure of Example 1A Parts D and E except substituting the above Part C alcohol for the Example 1A Part C alcohol, the title compound is obtained.

E.
(1α,2β,3β,4α)-5-[[2-[3-[2-(Hexyloxy)ethyl]-7-oxabicyclo[2.2.1]hept-2-yl]ethyl]thio]-N-hydroxy-N-methylpentanamide Following the procedure of Example 1 Part R except substituting the above Part D acid for the Example 1 Part Q acid, the title compound is obtained.

EXAMPLE 17

(1α,2β,3β,4α)-4-[2-[3-[2-(Hexylthio)ethyl]-7-oxabicyclo[2.2.1]hept-2-yl]ethoxy]-N-hydroxy-N-methylbutanamide A.
(1α,2β,3β,4α)-4-[2-[3-[(2-Hydroxy)ethyl]-7-oxabicyclo[2.2.1]hept-2-yl]ethoxy]butanoic acid, methyl ester Following the procedure of Example 11 Parts A, B and C except substituting (1α,2β,3β,4α)-4-[2-[3-hydroxymethyl)-7-oxabicyclo[2.2.1]hept-2-yl]ethoxy]butanoic acid, methyl ester (prepared as described in Example 7 Part H) for the Example 3 Part F alcohol, the title compound is obtained.

B.
(1α,2β,3β,4α)-4-[2-[3-[2-(Hexylthio)ethyl]-7-oxabicyclo[2.2.1]hept-2-yl]ethoxy]butanoic acid Following the procedure of Example 13 except substituting (1α,2β,3β,4α)-4-[2-[3-[2-(hydroxy)ethyl]-7-oxabicyclo[2.2.1]hept-2-yl]ethoxy]butanoic acid, methyl ester for the Example 11 Part C alcohol, the title compound is obtained.

C.
(1α,2β,3β,4α)-4-[2-[3-[2-(Hexylthio)ethyl]-7-oxabicyclo[2.2.1]hept-2-yl]ethoxy]-N-hydroxy-N-methylbutanamide Following the procedure of Example 1 Part R except substituting the above Part B acid for the Example 1 Part Q acid, the title compound is obtained.

EXAMPLE 18
(1α,2β,3β,4α)-5-[[2-[3-[2-(Hexylthio)ethyl]-7-oxabicyclo[2.2.1]hept-2-yl]ethyl]thio]-N-hydroxy-N-methylpentanamide

A.
(1α,2β,3β,4α)-5-[[2-[3-[2-(Hydroxy)ethyl]-7-oxabicyclo[2.2.1]hept-2-yl]ethyl]thio]pentanoic acid, methyl ester Following the procedure of Example 12 Part A except substituting (1α,2β,3β,4α)-5-[2-[3-(hydroxymethyl)-7-oxabicyclo[2.2.1]hept-2-yl]ethyl]thio]pentanoic acid, methyl and ethyl esters (prepared as described in Example 6 Part K) for the Example 1A Part C alcohol, the title compound is obtained.

B.
(1α,2β,3β,4α)-5-[[2-[3-[2(Hexylthio)ethyl]-7-oxabicyclo[2.2.1]hept-2-yl]ethyl]thio]pentanoic acid Following the procedure of Example 14 except substituting the above title A alcohol for the Example 12 Part A alcohol, the title compound is obtained.

C.
(1α,2β,3β,4α)-5-[[2-[3-[2-(Hexylthio)ethyl]-7-oxabicyclo[2.2.1]hept-2-yl]ethyl]thio]-N-hydroxy-N-methylpentanamide Following the procedure of Example 1 Part R except substituting the above Part B acid for the Example 1 Part Q acid, the title compound is obtained.

EXAMPLE 19
(1α,2β,3β,4α)-5-[[[3-(Methoxymethyl)-7-oxabicyclo[2.2.1]hept-2-yl]methoxy]-N-hydroxy-N-methylpentanamide Following the procedure of Example 3 except substituting methyl mesylate for hexyl mesylate, the title compound is obtained.

EXAMPLE 20
(1α,2β,3β,4α)-5-[[3-[(2-Propenyloxy)methyl]-7-oxabicyclo[2.2.1]hept-2-yl]methoxy]-N-hydroxy-N-methylpentanamide Following the procedure of Example 3 except substituting 2-propenyl mesylate for hexyl mesylate, the title compound is obtained.

EXAMPLE 21
(1α,2β,3β,4α)-5-[[3-(2-Butenyloxy)methyl]-7-oxabicyclo[2.2.1]hept-2-yl]methoxy]-N-hydroxy-N-methylpentanamide Following the procedure of Example 3 except substituting 2-butenyl mesylate for hexyl mesylate, the title compound is obtained.

EXAMPLE 22
(1α,2β,3β,4α)-5-[[3-[(Benzyloxy)methyl]-7-oxabicyclo[2.2.1]hept-2-yl]methoxy]-N-hydroxy-N-methylpentanamide Following the procedure of Example 3 except substituting benzyl mesylate for hexyl mesylate, the title compound is obtained.

EXAMPLE 23
(1α,2β,3β,4α)-5-[[3-[(Phenyloxy)methyl]-7-oxabicyclo[2.2.1]hept-2-yl]methoxy]-N-hydroxy-N-methylpentanamide (a) Phenol (1 mmol) is added to a solution of triphenylphosphine (1 mmol), diethylazodicarboxylate (1 mmol) and title F alcohol from Example 3 (1 mmol) in 25 ml THF and is stirred under an argon atmosphere for 48 hours at 23° C. The reaction mixture is concentrated in vacuo. The residue is triturated with ether and the solids are removed. The filtrate is concentrated in vacuo and chromatographed on silica gel to give (1α,2β,3β,4α)-5-[[3-[(phenyloxy)methyl]-7-oxabicyclo[2.2.1]hept-2-yl]methoxy]pentanoic acid, methyl ester.

(b) Following the procedure as set out in Example 3, the ester from part (a) is converted to the title compound.

EXAMPLE 24
(1α,2β,3β,4α)-5-[[3-[(Cyclohexyloxy)methyl]-7-oxabicyclo[2.2.1]hept-2-yl]methoxy]-N-hydroxy-N-methylpentanamide Following the procedure of Example 3 except substituting cyclohexylmesylate for hexyl mesylate, the title compound is obtained.

EXAMPLE 25
(1α,2β,3β,4α)-5-[[3-[(Cyclopentylmethoxy)methyl]-7-oxabicyclo[2.2.1]hept-2-yl]methoxy]-N-hydroxy-N-methylpentanamide Following the procedure of Example 3 except substituting cyclopentylmethyl mesylate for hexyl mesylate, the title compound is obtained.

EXAMPLE 26
(1α,2β,3β,4α)-5-[[[3-[(Benzyloxy)methyl]-7-oxabicyclo[2.2.1]hept-2-yl]methyl]thio]-N-hydroxy-N-methylpentanamide Following the procedure of Example 1A except substituting benzyl mesylate for hexyl mesylate, the title compound is obtained.

EXAMPLE 27

(1α,2β,3β,4α)-5-[[[3-[(2-Butenyloxy)methyl]-7-oxabicyclo[2.2.1]hept-2-yl]methyl]thio]-N-hydroxy-N-methylpentanamide Following the procedure of Example 1A except substituting 2-butenyl mesylate for hexyl mesylate, the title compound is obtained.

EXAMPLE 28

(1α,2β,3β,4α)-5-[[[3-[(Cyclohexyloxy)methyl]-7-oxabicyclo[2.2.1]hept-2-yl]methyl]thio]-N-hydroxy-N-methylpentanamide Following the procedure of Example 1A except substituting cyclohexyl mesylate mesylate for hexyl mesylate, the title compound is obtained.

EXAMPLE 29

(1α,2β,3β,4α)-5-[[[3-[(Cyclopentylmethyloxy)methyl]-7-oxabicyclo[2.2.1]hept-2-yl]methyl]thio]-N-hydroxy-N-methylpentanamide Following the procedure of Example 1A except substituting cyclopentylmethyl mesylate for hexyl mesylate, the title compound is obtained.

EXAMPLE 30

(1α,2β,3β,4α)-5-[[[3-[(Phenyloxy)methyl]-7-oxabicyclo[2.2.1]hept-2-yl]methyl]thio]-N-hydroxy-N-methylpentanamide Following the procedure of Examples 23 and 1A except substituting the Example 1A Part C alcohol for the Example 23 Part A alcohol, the title compound is obtained.

EXAMPLE 31

(1α,2β,3β,4α)-5-[[3-[(2-Pentylthio)methyl]-7-oxabicyclo[2.2.1]hept-2-yl]methoxy]-N-hydroxy-N-methylpentanamide Following the procedure of Example 4 except substituting 2-pentanethiol for 1-hexanethiol, the title compound is obtained.

EXAMPLE 32

(1α,2β,3β,4α)-5-[[3-[(Benzylthio)methyl]-7-oxabicyclo[2.2.1]hept-2-yl]methoxy]-N-hydroxy-N-methylpentanamide Following the procedure of Example 4 except substituting benzylmercaptan for 1-hexanethiol, the title compound is obtained.

EXAMPLE 33

(1α,2β,3β,4α)-5-[[3-[(Cyclohexylthio)methyl]-7-oxabicyclo[2.2.1]hept-2-yl]methoxy]-N-hydroxy-N-methylpentanamide Following the procedure of Example 4 except substituting cyclohexanethiol for 1-hexanethiol, the title compound is obtained.

EXAMPLE 34

(1α,2β,3β,4α)-5-[[3-[(Phenylthio)methyl]-7-oxabicyclo[2.2.1]hept-2-yl]methoxy]-N-hydroxy-N-methylpentanamide Following the procedure of Example 4 except substituting phenylmercaptan for 1-hexanethiol, the title compound is obtained.

EXAMPLE 35

(1α,2β,3β,4α)-5-[[[3-[(Cyclopentylthio)methyl]-7-oxabicyclo[2.2.1]hept-2-yl]methyl]thio]-N-hydroxy-N-methylpentanamide Following the procedure of Example 5 except substituting cyclopentylmercaptan for 1-hexanethiol, the title compound is obtained.

EXAMPLE 36

(1α,2β,3β,4α)-5-[[[3-[(Cyclohexylmethylthio)methyl]-7-oxabicyclo[2.2.1]hept-2-yl]methyl]thio]-N-hydroxy-N-methylpentanamide Following the procedure of Example 5 except substituting cyclohexylmethylmercaptan for 1-hexanethiol, the title compound is obtained.

EXAMPLE 37

(1α,2β,3β,4α)-5-[[[3-[(Phenylthio)methyl]-7-oxabicyclo[2.2.1]hept-2-yl]methyl]thio]-N-hydroxy-N-methylpentanamide Following the procedure of Example 5 except substituting phenylmercaptan for 1-hexanethiol, the title compound is obtained.

EXAMPLE 38

(1α,2β,3β,4α)-5-[[[3-[(Benzylthio)methyl]-7-oxabicyclo[2.2.1]hept-2-yl]methyl]thio]-N-hydroxy-N-methylpentanamide Following the procedure of Example 5 except substituting benzylmercaptan for 1-hexanethiol, the title compound is obtained.

EXAMPLE 39

(1α,2β,3β,4α)-5-[[[3-[(3-Pentenylthio)methyl]-7-oxabicyclo[2.2.1]hept-2-yl]methyl]thio]-N-hydroxy-N-methylpentanamide Following the procedure of Example 5 except substituting 1-(3-pentenyl)mercaptan for 1-hexanethiol, the title compound is obtained.

EXAMPLE 40

(1α,2β,3β,4α)-5-[[[3-[(Cyclohexyloxy)methyl]-7-oxabicyclo[2.2.1]hept-2-yl]ethyl]thio]-N-hydroxy-N-methylpentanamide Following the procedure of Example 6 except substituting cyclohexyl mesylate for hexyl mesylate, the title compound is obtained.

EXAMPLE 41

(1α,2β,3β,4α)-5-[[2-[3-[[(Cyclopentylmethyl)oxy]methyl]-7-oxabicyclo[2.2.1]hept-2-yl]ethyl]thio]-N-hydroxy-N-methylpentanamide Following the procedure of Example 6 except substituting cyclopentylmethyl mesylate for hexyl mesylate, the title compound is obtained.

EXAMPLE 42

(1α,2β,3β,4α)-5-[[2-[3-[(2-Butenyloxy)methyl]-7-oxabicyclo[2.2.1]hept-2-yl]ethyl]thio]-N-hydroxy-N-methylpentanamide Following the procedure of Example 6 except substituting 2-butenyl mesylate for hexyl mesylate, the title compound is obtained.

EXAMPLE 43

(1α,2β,3β,4α)-5-[[2-[3-[(Phenyloxy)methyl]-7-oxabicyclo[2.2.1]hept-2-yl]ethyl]thio]-N-hydroxy-N-methylpentanamide Following the procedure of Examples 23 and 1A except substituting the Example 6 Part K alcohol for the Example 3 Part F alcohol, the title compound is obtained.

EXAMPLE 44

(1α,2β,3β,4α)-4-[2-[3-[(Cyclohexyloxy)methyl]-7-oxabicyclo[2.2.1]hept-2-yl]ethoxy]-N-hydroxy-N-methylbutanamide Following the procedure of Example 7 except substituting cyclohexyl mesylate for hexyl mesylate, the title compound is obtained.

EXAMPLE 45

(1α,2β,3β,4α)-4-[2-[3-[(2-Pentenyloxy)methyl]-7-oxabicyclo[2.2.1]hept-2-yl]ethoxy]-N-hydroxy-N-methylbutanamide Following the procedure of Example 7 except substituting 2-pentenyl mesylate for hexyl mesylate, the title compound is obtained.

EXAMPLE 46

(1α,2β,3β,4α)-4-[2-[3-[(Benzyloxy)methyl]-7-oxabicyclo[2.2.1]hept-2-yl]ethoxy]-N-hydroxy-N-methylbutanamide Following the procedure of Example 7 except substituting benzyl mesylate for hexyl mesylate, the title compound is obtained.

EXAMPLE 47

(1α,2β,3β,4α)-4-[2-[3-[(Phenyloxy)methyl]-7-oxabicyclo[2.2.1]hept-2-yl]ethoxy]-N-hydroxy-N-methylbutanamide Following the procedure of Examples 23 and 7 except substituting the Example 7 Part H alcohol for the Example 3 Part F alcohol, the title compound is obtained.

EXAMPLE 48

(1α,2β,3β,4α)-4-[2-[3-[(Cyclopentylmethyloxy)methyl]-7-oxabicyclo[2.2.1]hept-2-yl]ethoxy]-N-hydroxy-N-methylbutanamide Following the procedure of Example 7 except substituting cyclopentylmethyl mesylate for hexyl mesylate, the title compound is obtained.

EXAMPLE 49

(1α,2β,3β,4α)-5-[[2-[3-[(Benzylthio)methyl]-7-oxabicyclo[2.2.1]hept-2-yl]ethyl]thio]-N-hydroxy-N-methylpentanamide Following the procedure of Example 9 except substituting benzylmercaptan for 1-hexanethiol, the title compound is obtained.

EXAMPLE 50

(1α,2β,3β,4α)-5-[[2-[3-[(Phenylthio)methyl]-7-oxabicyclo[2.2.1]hept-2-yl]ethyl]thio]-N-hydroxy-N-methylpentanamide Following the procedure of Example 9 except substituting phenylmercaptan for 1-hexanethiol, the title compound is obtained.

EXAMPLE 51

(1α,2β,3β,4α)-5-[[2-[3-[(Cycloheptylthio)methyl]-7-oxabicyclo[2.2.1]hept-2-yl]ethyl]thio]-N-hydroxy-N-methylpentanamide Following the procedure of Example 9 except substituting cycloheptylmercaptan for 1-hexanethiol, the title compound is obtained.

EXAMPLE 52

(1α,2β,3β,4α)-5-[[2-[3-[(Cyclohexylmethylthio)methyl]-7-oxabicyclo[2.2.1]hept-2-yl]ethyl]thio]-N-hydroxy-N-methylpentanamide Following the procedure of Example 9 except substituting cyclohexylmethylmercaptan for 1-hexanethiol, the title compound is obtained.

EXAMPLE 53

(1α,2β,3β,4α)-5-[[2-[3-[(2-Propenylthio)methyl]-7-oxabicyclo[2.2.1]hept-2-yl]ethyl]thio]-N-hydroxy-N-methylpentanamide Following the procedure of Example 9 except substituting 2-propenylthiol for 1-hexanethiol, the title compound is obtained.

EXAMPLE 54

(1α,2β,3β,4α)-4-[2-[3-[(Benzylthio)methyl]-7-oxabicyclo[2.2.1]hept-2-yl]ethoxy]-N-hydroxy-N-methylbutanamide Following the procedure of Example 10 except substituting benzylmercaptan for 1-hexanethiol, the title compound is obtained.

EXAMPLE 55

(1α,2β,3β,4α)-4-[2-[3-[(Phenylthio)methyl]-7-oxabicyclo[2.2.1]hept-2-yl]ethoxy]-N-hydroxy-N-methylbutanamide Following the procedure of Example 10 except substituting phenylmercaptan for 1-hexanethiol, the title compound is obtained.

EXAMPLE 56

(1α,2β,3β,4α)-4-[2-[3-[(3-Pentenylthio)methyl]-7-oxabicyclo[2.2.1]hept-2-yl]ethoxy]-N-hydroxy-N-methylbutanamide Following the procedure of Example 10 except substituting 3-pentenylthiol for 1-hexanethiol, the title compound is obtained.

EXAMPLE 57

(1α,2β,3β,4α)-4-[2-[3-[(Cyclohexylthio)methyl]-7-oxabicyclo[2.2.1]hept-2-yl]ethoxy]-N-hydroxy-N-methylbutanamide Following the procedure of Example 11 except substituting cyclohexylmercaptan for 1-hexanethiol, the title compound is obtained.

EXAMPLE 58

(1α,2β,3β,4α)-5-[[3-[2-(Benzyloxy)ethyl]-7-oxabicyclo[2.2.1]hept-2-yl]methoxy]-N-hydroxy-N-methylpentanamide Following the procedure of Example 10 except substituting benzyl mesylate for hexyl mesylate, the title compound is obtained.

EXAMPLE 59

(1α,2β,3β,4α)-5-[[3-[2-(Phenyloxy)ethyl]-7-oxabicyclo[2.2.1]hept-2-yl]methoxy]-N-hydroxy-N-methylpentanamide Following the procedure of Example 11 except substituting phenyl mesylate for hexyl mesylate, the title compound is obtained.

EXAMPLE 60

(1α,2β,3β,4α)-5-[[3-[2-(3-Butenyloxy)ethyl]-7-oxabicyclo[2.2.1]hept-2-yl]methoxy]-N-hydroxy-N-methylpentanamide Following the procedure of Example 11 except substituting 1-butenyl mesylate for hexyl mesylate, the title compound is obtained.

EXAMPLE 61

(1α,2β,3β,4α)-5-[[3-[2-(Cyclohexyloxy)ethyl]-7-oxabicyclo[2.2.1]hept-2-yl]methoxy]-N-hydroxy-N-methylpentanamide Following the procedure of Example 11 except substituting cyclohexyl mesylate for hexyl mesylate, the title compound is obtained.

EXAMPLE 62

(1α,2β,3β,4α)-5-[[3-[2-(Propyloxy)ethyl]-7-oxabicyclo[2.2.1]hept-2-yl]methoxy]-N-hydroxy-N-methylpentanamide Following the procedure of Example 11 except substituting n-propyl mesylate for hexyl mesylate, the title compound is obtained.

EXAMPLE 63

(1α,2β,3β,4α)-5-[[[3-[2-(Benzyloxy)ethyl]-7-oxabicyclo[2.2.1]hept-2-yl]methyl]thio]-N-hydroxy-N-methylpentanamide Following the procedure of Example 12 except substituting benzyl mesylate for hexyl mesylate, the title compound is obtained.

EXAMPLE 64

(1α,2β,3β,4α)-5-[[[3-[2-(Phenyloxy)ethyl]-7-oxabicyclo[2.2.1]hept-2-yl]methyl]-thio]-N-hydroxy-N-methylpentanamide Following the procedure of Example 23 except substituting the Example 12 Part A alcohol for the Example 3 Part F alcohol, the title compound is obtained.

EXAMPLE 65

(1α,2β,3β,4α)-5-[[[3-[2-(Cyclohexyloxy)ethyl]-7-oxabicyclo[2.2.1]hept-2-yl]methyl]thio]-N-hydroxy-N-methylpentanamide Following the procedure of Example 12 except substituting cyclohexyl mesylate for hexyl mesylate, the title compound is obtained.

EXAMPLE 66

(1α,2β,3β,4α)-5-[[[3-[2-(Cyclopentylmethyloxy)ethyl]-7-oxabicyclo[2.2.1]hept-2-yl]methyl]thio]-N-hydroxy-N-methylpentanamide Following the procedure of Example 12 except substituting cyclopentylmethyl mesylate for hexyl mesylate, the title compound is obtained.

EXAMPLE 67

(1α,2β,3β,4α)-5-[[[3-[2-(2-Pentenyloxy)ethyl]-7-oxabicyclo[2.2.1]hept-2-yl]methyl]thio]-N-hydroxy-N-methylpentanamide Following the procedure of Example 12 except substituting 2-pentenyl mesylate for hexyl mesylate, the title compound is obtained.

EXAMPLE 68

(1α,2β,3β,4α)-5-[[3-[2-(Pentylthio)ethyl]-7-oxabicyclo[2.2.1]hept-2-yl]methoxy]-N-hydroxy-N-methylpentanamide Following the procedure of Example 13 except substituting 1-pentanethiol for 1-hexanethiol, the title compound is obtained.

EXAMPLE 69

(1α,2β,3β,4α)-5-[[3-[2-(Benzylthio)ethyl]-7-oxabicyclo[2.2.1]hept-2-yl]methoxy]-N-hydroxy-N-methylpentanamide Following the procedure of Example 13 except substituting benzylthiol for 1-hexanethiol, the title compound is obtained.

EXAMPLE 70

(1α,2β,3β,4α)-5-[[3-[2-(Phenylthio)ethyl]-7-oxabicyclo[2.2.1]hept-2-yl]methoxy]-N-hydroxy-N-methylpentanamide Following the procedure of Example 13 except substituting phenylmercaptan for 1-hexanethiol, the title compound is obtained.

EXAMPLE 71

(1α,2β,3β,4α)-5-[[3-[2-(Cyclohexylthio)ethyl]-7-oxabicyclo[2.2.1]hept-2-yl]methoxy]-N-hydroxy-N-methylpentanamide Following the procedure of Example 13 except substituting cyclohexylmercaptan for 1-hexanethiol, the title compound is obtained.

EXAMPLE 72

(1α,2β,3β,4α)-5-[[[3-[2-(Benzylthio)ethyl]-7-oxabicyclo[2.2.1]hept-2-yl]methyl]thio]-N-hydroxy-N-methylpentanamide Following the procedure of Example 14 except substituting benzylmercaptan for 1-hexanethiol, the title compound is obtained.

EXAMPLE 73

(1α,2β,3β,4α)-5-[[[3-[2-(Cycloheptylthio)ethyl]-7-oxabicyclo[2.2.1]hept-2-yl]methyl]thio]-N-hydroxy-N-methylpentanamide Following the procedure of Example 14 except substituting cycloheptylmercaptan for 1-hexanethiol, the title compound is obtained.

EXAMPLE 74

(1α,2β,3β,4α)-5-[[[3-[2-(Phenylthio)ethyl]-7-oxabicyclo[2.2.1]hept-2-yl]methyl]thio]-N-hydroxy-N-methylpentanamide Following the procedure of Example 14 except substituting phenylmercaptan for 1-hexanethiol, the title compound is obtained.

EXAMPLE 75

(1α,2β,3β,4α)-5-[[[3-[2-(Cyclohexylmethylthio)ethyl]-7-oxabicyclo[2.2.1]hept-2-yl]methyl]thio]-N-hydroxy-N-methylpentanamide Following the procedure of Example 14 except substituting cyclohexylmethylmercaptan for 1-hexanethiol, the title compound is obtained.

EXAMPLE 76

(1α,2β,3β,4α)-5-[[[3-[2-(2-Propenylthio)ethyl]-7-oxabicyclo[2.2.1]hept-2-yl]methyl]thio]-N-hydroxy-N-methylpentanamide Following the procedure of Example 14 except substituting 1-(2-propenyl)thiol for 1-hexanethiol, the title compound is obtained.

EXAMPLE 77

(1α,2β,3β,4α)-4-[2-[3-[2-(Heptyloxy)ethyl]-7-oxabicyclo[2.2.1]hept-2-yl]ethoxy]-N-hydroxy-N-methylbutanamide Following the procedure of Example 15 except substituting heptyl mesylate for hexyl mesylate, the title compound is obtained.

EXAMPLE 78

(1α,2β,3β,4α)-4-[2-[3-[2-(Benzyloxy)ethyl]-7-oxabicyclo[2.2.1]hept-2-yl]ethoxy]-N-hydroxy-N-methylbutanamide Following the procedure of Example 15 except substituting benzyl mesylate for hexyl mesylate, the title compound is obtained.

EXAMPLE 79

(1α,2β,3β,4α)-4-[2-[3-[2-(Phenyloxy)ethyl]-7-oxabicyclo[2.2.1]hept-2-yl]ethoxy]-N-hydroxy-N-methylbutanamide Following the procedure of Example 15 except substituting phenyl mesylate for hexyl mesylate, the title compound is obtained.

EXAMPLE 80

(1α,2β,3β,4α)-4-[2-[3-[2-(Cyclohexyloxy)ethyl]-7-oxabicyclo[2.2.1]hept-2-yl]ethoxy]-N-hydroxy-N-methylbutanamide Following the procedure of Example 15 except substituting cyclohexyl mesylate for hexyl mesylate, the title compound is obtained.

EXAMPLE 81

(1α,2β,3β,4α)-4-[2-[3-[2-(2-Cyclopentylethyloxy)ethyl]-7-oxabicyclo[2.2.1]hept-2-yl]ethoxy]-N-hydroxy-N-methylbutanamide Following the procedure of Example 15 except substituting cyclopentylethyl mesylate for hexyl mesylate, the title compound is obtained.

EXAMPLE 82

(1α,2β,3β,4α)-5-[[2-[3-[2-(Benzyloxy)ethyl]-7-oxabicyclo[2.2.1]hept-2-yl]ethyl]thio]-N-hydroxy-N-methylpentanamide Following the procedure of Example 16 except substituting benzyl mesylate for hexyl mesylate, the title compound is obtained.

EXAMPLE 83

(1α,2β,3β,4α)-5-[[2-[3-[2-(Phenyloxy)ethyl]-7-oxabicyclo[2.2.1]hept-2-yl]ethyl]thio]-N-hydroxy-N-methylpentanamide Following the procedure of Example 23 except substituting the Example 16 Part C alcohol for the Example 1 Part F alcohol, the title compound is obtained.

EXAMPLE 84

(1α,2β,3β,4α)-5-[[2-[3-[2-(Cyclopentyloxy)ethyl]-7-oxabicyclo[2.2.1]hept-2-yl]ethyl]thio]-N-hydroxy-N-methylpentanamide Following the procedure of Example 16 except substituting cyclopentyl mesylate for hexyl mesylate, the title compound is obtained.

EXAMPLE 85

(1α,2β,3β,4α)-4-[[2-[3-[2-(3-Hexenyloxy)ethyl]-7-oxabicyclo[2.2.1]hept-2-yl]ethyl]thio]-N-hydroxy-N-methylpentanamide Following the procedure of Example 16 except substituting 3-hexenyl mesylate for hexyl mesylate, the title compound is obtained.

EXAMPLE 86

(1α,2β,3β,4α)-4-[[2-[3-[2-(Cyclopropylmethyloxy)ethyl]-7-oxabicyclo[2.2.1]hept-2-yl]ethyl]thio]-N-hydroxy-N-methylpentanamide Following the procedure of Example 16 except substituting cyclopropylmethyl mesylate for hexyl mesylate, the title compound is obtained.

EXAMPLE 87

(1α,2β,3β,4α)-4-[2-[3-[2-(Benzyltho)ethyl]-7-oxabicyclo[2.2.1]hept-2-yl]ethoxy]-N-hydroxy-N-methylbutanamide Following the procedure of Example 17 except substituting benzylmercaptan for 1-hexanethiol, the title compound is obtained.

EXAMPLE 88

(1α,2β,3β,4α)-4-[2-[3-[2-(Phenylthio)ethyl]-7-oxabicyclo[2.2.1]hept-2-yl]ethoxy]-N-hydroxy-N-methylbutanamide Following the procedure of Example 17 except substituting phenylmercaptan for 1-hexanethiol, the title compound is obtained.

EXAMPLE 89

(1α,2β,3β,4α)-4-[2-[3-[2-(Cyclohexylthio)ethyl]-7-oxabicyclo[2.2.1]hept-2-yl]ethoxy]-N-hydroxy-N-methylbutanamide Following the procedure of Example 17 except substituting cyclohexylmercaptan for 1-hexanethiol, the title compound is obtained.

EXAMPLE 90

(1α,2β,3β,4α)-4-[2-[3-[2-(2-Heptenylthio)ethyl]-7-oxabicyclo[2.2.1]hept-2-yl]ethoxy]-N-hydroxy-N-methylbutanamide Following the procedure of Example 17 except substituting 1-(2-heptenyl)thiol for 1-hexanethiol, the title compound is obtained.

EXAMPLE 91

(1α,2β,3β,4α)-4-[2-[3-[2-(Cyclopentylmethylthio)ethyl]-7-oxabicyclo[2.2.1]hept-2-yl]ethoxy]-N-hydroxy-N-methylbutanamide Following the procedure of Example 17 except substituting cyclopentylmethylmercaptan for 1-hexanethiol, the title compound is obtained.

EXAMPLE 92

(1α,2β,3β,4α)-5-[[2-[3-[2-(Benzylthio)ethyl]-7-oxabicyclo[2.2.1]hept-2-yl]ethyl]thio]-N-hydroxy-N-methylpentanamide Following the procedure of Example 18 except substituting benzylmercaptan for 1-hexanethiol, the title compound is obtained.

EXAMPLE 93

(1α,2β,3β,4α)-5-[[2-[3-[2-(Phenylthio)ethyl]-7-oxabicyclo[2.2.1]hept-2-yl[ethyl]thio]-N-hydroxy-N-methylpentanamide Following the procedure of Example 18 except substituting phenylmercaptan for 1-hexanethio, the title compound is obtained.

EXAMPLE 94

(1α,2β,3β,4α)-5-[[2-[3-[2-(Cyclohexylthio)ethyl]-7-oxabicyclo[2.2.1]hept-2-yl]ethyl]thio]-N-hydroxy-N-methylpentanamide Following the procedure of Example 18 except substituting cyclohexylmercaptan for 1-hexanethiol, the title compound is obtained.

EXAMPLE 95

(1α,2β,3β,4α)-5-[[2-[3-[2-(2-Hexenylthio)ethyl]-7-oxabicyclo[2.2.1]hept-2-yl]ethyl]thio]-N-hydroxy-N-methylpentanamide Following the procedure of Example 18 except substituting 1-(2-hexenyl)thio for 1-hexanethiol, the title compound is obtained.

EXAMPLE 96

(1α,2β,3β,4α)-5-[[2-[3-[2-(Butylthio)ethyl]-7-oxabicyclo[2.2.1]hept-2-yl]ethyl]thio]-N-hydroxy-N-methylpentanamide Following the procedure of Example 18 except substituting 1-butanethiol for 1-hexanethiol, the title compound is obtained.

EXAMPLE 97

(1α,2β,3β,4α)-5-[[3-[4-(Hexyloxy)butyl]-7-oxabicyclo[2.2.1]hept-2-yl]methoxy]-N-hydroxy-N-methylpentanamide

A.

(1α,2β,3β,4α)-5-[3-(3-Oxo)propyl]-7-oxabicyclo[2.2.1]hept-2-yl]methoxy]pentanoic acid, methyl ester Following the procedure of Example 11 Part B except substituting (1α,2β,3β,4α)-5-[3-(2-oxo)ethyl-7-oxabicyclo[2.2.1]hept-2-yl]methoxy]pentanoic acid, methyl ester for (1α,2β,3β,4α)-7-[3-formyl-7-oxabicyclo[2.2.1]hept-2-yl]methoxy]pentanoic acid, methyl ester, the title A compound is obtained.

B.

(1α,2β,3β,4α)-5-[[3-(4-Oxo)butyl-7-oxabicyclo[2.2.1]hept-2-yl]methoxy]pentanoic acid, methyl ester Following the procedure of Example 16 Part B except substituting the aldehyde from Part A above for (1α,2β,3β,4α)-5-[3-formyl-7-oxabicyclo[2.2.1]hept-2-yl]methoxy]pentanoic acid, methyl ester, the title B aldehyde is obtained.

C.

(1α,2β,3β,4α)-5-[[3-(4-Hydroxybutyl)-7-oxabicyclo[2.2.1]hept-2-yl]methoxy]pentanoic acid, methyl ester Following the procedure of Example 11 Part C except substituting the title B aldehyde for (1α,2β,3β,4α)-5-[3-(2-oxo)ethyl-7-oxabicyclo[2.2.1]hept-2-yl]methoxy]pentanoic acid, methyl ester, the title C alcohol is obtained.

D.

(1α,2β,3β,4α)-5-[[3-[4-(Hexyloxy)butyl-7-oxabicyclo[2.2.1]hept-2-yl]methoxy]pentanoic acid Following the procedure of Example 3 except substituting the above part C alcohol for the alcohol used in Example 3 Part G, the title compound is obtained.

E.

(1α,2β,3β,4α)-5-[[3-[4-(Hexyloxy)butyl]-7-oxabicyclo[2.2.1]hept-2-yl]methoxy]-N-hydroxy-N-methylpentanamide Following the procedure of Example 1 Part R except substituting the above Part D acid for the Example 1 Part Q acid, the title compound is obtained.

EXAMPLE 98

(1α,2β,3β,4α)-5-[[[3-[4-(Benzyloxy)butyl]-7-oxabicyclo[2.2.1]hept-2-yl]methyl]thio]-N-hydroxy-N-methylpentanamide Following the procedure of Examples 97 and 12 except substituting the Example 97 Part C alcohol for the Example 12 Part A alcohol and substituting benzyl mesylate for hexyl mesylate, the title compound is obtained.

EXAMPLE 99

(1α,2β,3β,4α)-5-[3-[4-(Cyclohexylthio)butyl]-7-oxabicyclo[2.2.1]hept-2-yl]methoxy]-N-hydroxy-N-methylpentanamide Following the procedure of Examples 97 and 12 except substituting the Example 97 Part C alcohol for the Example 11 Part C alcohol and substituting cyclohexylmercaptan for 1-hexanethiol, the title compound is obtained.

EXAMPLE 100

(1α,2β,3β,4α)-5-[[[3-[4-(Hexylthio)butyl]-7-oxabicyclo[2.2.1]-hept-2-yl]methyl]thio]-N-hydroxy-N-methylpentanamide

A.

(1α,2β,3β,4α)-5-[[[3-(3-Oxo)propyl-7-oxabicyclo[2.2.1]hept-2-yl]methyl]thio]pentanoic acid, methyl ester Following the procedure of Example 14 Part B except substituting (1α,2β,3β,4α)-5-[[[3-(2-oxo)ethyl-7-oxabicyclo[2.2.1]hept-2-yl]methyl]thio]pentanoic acid, methyl ester for (1α,2β,3β,4α)-5-[[[3-formyl-7-oxabicyclo[2.2.1]hept-2-yl]methyl]thio]pentanoic acid, methyl ester, the title A compound is obtained.

B.

(1α,2β,3β,4α)-5-[[[3-(4-Oxo)butyl-7-oxabicyclo[2.2.1]hept-2-yl]methyl]thio]pentanoic acid, methyl ester Following the procedure of Example 14 Part B except substituting the aldehyde from Part A above for (1α,2β,3β,4α)-5-[[[3-formyl-7-oxabicyclo[2.2.1]hept-2-yl]methyl]thio]pentanoic acid, methyl ester, the title B aldehyde is obtained.

C.

(1α,2β,3β,4α)-5-[[[3-(4-Hydroxybutyl)-7-oxabicyclo[2.2.1]hept-2-yl]methyl]thio]pentanoic acid, methyl ester Following the procedure of Example 14 Part C except substituting the title B aldehyde for (1α,2β,3β,4α)-5-[[[3-(2-oxo)ethyl-7-oxabicyclo[2.2.1]hept-2-yl]methyl]thio]pentanoic acid, methyl ester, the title C alcohol is obtained.

D.

(1α,2β,3β,4α)-5-[[[3-[4-(Hexylthio)butyl]-7-oxabicyclo[2.2.1]hept-2-yl]methyl]thio]pentanoic acid Following the procedure of Example 1A except substituting the above Part C alcohol for the alcohol used in Example 1A, the title compound is obtained.

E.

(1α,2β,3β,4α)-5-[[[3-[4-(Hexylthio)butyl]-7-oxabicyclo[2.2.1]hept-2-yl]methyl]thio]-N-hydroxy-N-methylpentanamide Following the procedure of Example 1 Part R except substituting the above Part D acid for the Example 1 Part Q acid, the title compound is obtained.

EXAMPLE 101

(1α,2β,3β,4α)-4-[2-[3-[4-(Hexyloxy)butyl]-7-oxabicyclo[2.2.1]hept-2-yl]ethoxy]-N-hydroxy-N-methylbutanamide Following the procedure of Examples 97 and 15 except substituting the Example 11 Part B aldehyde for the aldehyde used in Example 97 Part A, the title compound is obtained.

EXAMPLE 102

(1α,2β,3β,4α)-5-[[[3-[(4-Hexylthio)butyl]-7-oxabicyclo[2.2.1]hept-2-yl]methyl]thio]-N-hydroxy-N-phenylpentanamide Following the procedure of Example 1 Part R except substituting the Example 100 Part D acid for the Example 1 Part Q acid and N-phenylhydroxylamine for N-methylhydroxylamine, the title compound is obtained.

EXAMPLE 103

(1α,2β,3β,4α)-5-[[[3-[(4-Hexylthio)butyl]-7-oxabicyclo[2.2.1]hept-2-yl]methyl]thio]-N-hydroxy-N-benzylpentanamide Following the procedure of Example 1 Part R except substituting the Example 100 Part D acid for the Example 1 Part Q acid and N-benzylhydroxylamine for N-methylhydroxylamine, the title compound is obtained.

EXAMPLE 104

(1α,2β,3β,4α)-5-[[[3-[(4-Hexylthio)butyl]-7-oxabicyclo[2.2.1]hept-2-yl]methyl]thio]-N-hydroxy-N-cyclohexylpentanamide Following the procedure of Example 1 Part R except substituting the Example 100 Part D acid for the Example 1 Part Q acid and N-cyclohexylhydroxylamine for N-methylhydroxylamine, the title compound is obtained.

EXAMPLE 105

(1α,2β,3β,4α)-5-[[2-[3-[4-(Hexyloxy)butyl]-7-oxabicyclo[2.2.1]hept-2-yl]ethyl]thio]-N-hydroxy-N-methylpentanamide Following the procedure of Examples 97 and 16 except substituting the Example 16 Part B aldehyde for the aldehyde used in Example 97 Part A, the title compound is obtained.

EXAMPLE 106

(1α,2β,3β,4α)-4-[[2-[3-[4-(Hexylthio)butyl]-7-oxabicyclo[2.2.1]hept-2-yl]ethyl]thio]-N-hydroxy-N-methylpentanamide Following the procedure of Examples 100 and 18 except substituting the Example 18 Part A aldehyde for the aldehyde used in Example 100 Part A, the title compound is obtained.

EXAMPLE 107

(1α,2β,3β,4α)-5-[[3-[(Hexysulfinyl)methyl)methyl]-7-oxabicyclo[2.2.1]hept-2-yl]methoxy]-N-hydroxy-N-methylpentanamide

A.

(1α,2β,3β,4α)-5-[[3-[(Hexylsulfinyl)methyl]-7-oxabicyclo[2.2.1]hept-2-yl]methoxy]pentanoic acid, methyl ester and (1α,2β,3β,4α)-5-[[3-(Hexylsulfonyl)methyl-7-oxabicyclo[2.2.1]hept-2-yl]methoxy]pentanoic acid, methyl ester To a solution of 668 mg (1.72 mmol) of (1α,2β,3β,4α)-5-[[3-[(hexylthio)methyl]-7-oxabicyclo[2.2.1]hept-2-yl]methoxy]pentanoic acid, methyl ester (prepared as described in Example 4) in 6.78 ml of methanol at 0° C. is added dropwise over 4 minutes 8.37 ml of 0.5M aqueous sodium periodate solution. Tetrahydrofuran (2 ml) is then added and the resulting reaction mixture is stirred at room temperature for 15 hours. A white precipitate is removed by filtration and washed with ether (3×50 ml). The filtrate is washed with 60 ml of a saturated aqueous MaHCO$_3$ solution and dried over anhydrous magnesium sulfate. Concentration in vacuo affords 648 mg of an oily crude product. This is chromatographed on 50 g of silica gel 60 using 0.5–1.0% CH₃OH in ether to give the title compounds.

B. (1α,2β,3β,4α)-5-[[3-[(Hexylsulfonyl)methyl]-7-oxabicyclo[2.2.1]hept-2-yl]methoxy]pentanoic acid To a stirred solution of 165 mg (0.39 mmole) of the Part A sulfonyl compound in 20.3 ml of THF and 3.09 ml of H₂O under argon is added 3.90 ml of 1N aqueous lithium hydroxide solution. This mixture is purged with argon vigorously for 10 minutes and stirred at room temperature for 6 hours. The reaction mixture is acidified to pH 4 by addition of 1N aqueous HCl solution and poured into 30 ml of saturated NaCl solution. The resulting solution is saturated with solid NaCl and extracted with EtOAc (4×50 ml). The combined EtOAc extracts are dried (MgSO₄ anhydrous), filtered and concentrated in vacuo to give 165 mg of crude acid which is purified by flash chromatography to obtain 145 mg of pure acid.

C. (1α,2β,3β,4α)-5-[[3-[(Hexylsulfinyl)methyl]-7-oxabicyclo[2.2.1]hept-2-yl]methoxy]-N-hydroxy-N-methylpentanamide Following the procedure of Example 1 Part R except substituting the Part B acid for the Example 1 Part Q acid, the title compound is obtained.

EXAMPLE 108

(1α,2β,3β,4α)-5-[[3-[(Hexylsulfinyl)methyl]-7-oxabicyclo[2.2.1]hept-2-yl]methoxy]-N-hydroxy-N-methylpentanamide To a stirred solution of 142 mg (0.35 mmol) of Example 107 ester and sulfinyl ester in 27.0 ml of THF and 4.11 ml of H₂O under argon is added 5.19 ml of 1N aqueous lithium hydroxide solution. This mixture is purged with argon vigorously for 10 minutes and stirred at room temperature for 6 hours. The reaction mixture is acidified to pH 4 by addition of 1N aqueous HCl solution and poured into 50 ml of saturated NaCl solution. The resulting solution is saturated with solid NaCl and extracted with EtOAc (4×100 ml). The combined EtOAc extracts are dried (MgSO₄ anhydrous), filtered and concentrated in vacuo to give crude acid which is purified by flash chromatography.

The acid is then treated as described in Example 1 Part R to form the title compound.

EXAMPLES 109 TO 118

Following the procedures as outlined in the specification and as described in the working Examples, the following compounds may be prepared.

| Ex. No. | m | A | n | p | X | R² | R | R¹ |
|---|---|---|---|---|---|---|---|---|
| 109. | 1 | O | 2 | 1 | S | C₃H₇ | H | C₄H₉ |
| 110. | 2 | S | 1 | 2 | S | C₆H₅ | C₃H₇ | H |
| 111. | 1 | S | 4 | 3 | O | C₆H₄(CH₂)₂— | C₂H₅ | C₆H₅ |
| 112. | 2 | O | 5 | 2 | O | cyclopentyl | H | cyclohexyl |
| 113. | 1 | O | 3 | 4 | S(=O)₂ | cyclopentyl-CH₂— | C₄H₉-cyclopentyl | CH₃C(=O) |
| 114. | 2 | S | 6 | 5 | O | cyclohexyl | C₆H₅ | C₆H₅C(=O) |
| 115. | 1 | O₂S | 7 | 3 | O₂S | CH₂=CH—CH₂— | cyclohexyl | cyclopentyl-CH₂ |
| 116. | 2 | S | 8 | 2 | O | CH₃CH₂CHCH₂— | C₃H₇ | C₂H₅ |
| 117. | 1 | OS | 6 | 1 | OS | C₆H₁₃ | phenyl-CH₂ | H |

General structure: bicyclic core with (CH₂)ₘ—A—(CH₂)ₙ—C(=O)—N(R)—OR¹ and (CH₂)ₚ—X—R²

-continued

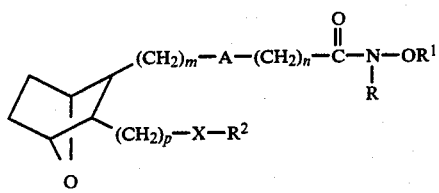

| Ex. No. | m | A | n | p | X | R² | R | R¹ |
|---|---|---|---|---|---|---|---|---|
| 118. | 2 | O | 5 | 2 | S | C₄H₉ | H | H |

What is claimed is:

1. A compound of the structure

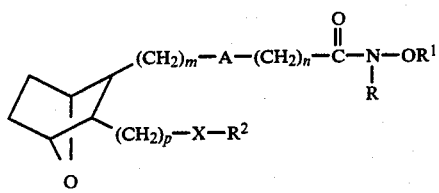

including all stereoisomers thereof, wherein A is O or

q is 0, 1 or 2; m is 1 or 2; n is 1 to 8; p is 1 to 5; X is O or

q' is 0, 1 or 2; wherein q' is 0, 1 or 2 wherein A is O, and q' is 0 when A is S; R is H, lower alkyl, aryl, arylalkyl, cycloalkyl or cycloalkylalkyl; R¹ is H, lower alkyl, aryl, arylalkyl, cycloalkyl, alkanoyl or aroyl; and R² is lower alkyl, aryl, arylalkyl, cycloalkyl, cycloalkylalkyl or lower alkenyl containing 2 to 12 carbons, wherein lower alkyl or alkyl alone or as part of another group contains 1 to 12 carbons and is unsubstituted or is substituted with halo, CF₃, alkoxy, aryl, alkyl-aryl, haloaryl, cycloalkyl, or alkylcycloalkyl;

aryl alone or as part of another group is phenyl or naphthyl which is unsubstituted or is substituted with 1 or 2 lower alkyl groups, halogens, and/or lower alkoxy groups;

cycloalkyl alone or as part of another group contains 3 to 12 carbons and is unsubstituted or is substituted with 1 or 2 halogens, 1 or 2 lower alkyl groups and/or 1 or 2 lower alkoxy groups; and (CH₂)ₘ, (CH₂)ₙ and (CH₂)ₚ may independently contain 1 or 2 lower alkyl and/or halo substituents.

2. The compound as defined in claim 1 wherein A is O and X is O.

3. The compound as defined in claim 1 wherein A is S and X is O.

4. The compound as defined in claim 1 wherein both A and X are S.

5. The compound as defined in claim 1 wherein A is O and X is S.

6. The compound as defined in claim 1 wherein m is 2 and p is 1.

7. The compound as defined in claim 1 wherein m is 1 and p is 1.

8. The compound as defined in claim 1 wherein n is 3 to 5.

9. The compound as defined in claim 1 wherein m is 1, A is O or S, p is 1, n is 3 to 5, R is H or lower alkyl, R¹ is H or lower alkyl and R² is lower alkyl.

10. The compound as defined in claim 1 wherein R² is butyl, pentyl, hexyl or heptyl including all isomers thereof.

11. The compound as defined in claim 1 having the name (1α,2β,3β,4α)-5-[[[3-[(hexyloxy)methyl]-7-oxabicyclo[2.2.1]hept-2-yl]methyl]thio]-N-hydroxy-N-methylpentanamide, including all stereoisomers thereof.

12. The compound as defined in claim 1 having the name (1α,2β,3β,4α)-5-[[2-[3-[(hexyloxy)methyl]-7-oxabicyclo[2.2.1]hept-2-yl]ethyl]thio]-N-hydroxy-N-methyl-4-butanamide, including all stereoisomers thereof.

13. A method of inhibiting Δ⁵-lipoxygenase, which comprises administering to the circulatory system of a mammalian host an effective amount of a compound as defined in claim 1 or a pharamaceutically acceptable salt thereof.

14. The method as defined in claim 13 wherein said compound is administered in an amount within the range of from about 1 to about 100 mg/kg.

15. A composition for inhibiting allergic conditions in a mammalian species, comprising an effective amount of a compound as defined in claim 1 or a pharmaceutically acceptable salt thereof, and a pharmaceutically acceptable carrier therefor.

16. A method of inhibiting or reducing inflammation or treating asthma, which comprises administering to a mammalian host an effective amount of a compound as defined in claim 1 or a pharmaceutically acceptable salt thereof.

17. A method for treating psoriasis, which comprises topically or systemically administering to a mammalian host an effective amount of a compound as defined in claim 1 or a pharmaceutically acceptable salt thereof.

* * * * *